US007888320B2

(12) United States Patent
Wakkach et al.

(10) Patent No.: US 7,888,320 B2
(45) Date of Patent: Feb. 15, 2011

(54) COMPOSITION FOR TREATING CANCER ADAPTED FOR INTRA-TUMORAL ADMINISTRATION AND USES THEREOF

(75) Inventors: Abdelilah Wakkach, Nice (FR); Claudine Blin-Wakkach, Nice (FR); David Momier, Nice (FR); Georges Carle, Nice (FR)

(73) Assignee: Centre National de la Recherche Scientifique - CNRS (FR)

( * ) Notice: Subject to any disclaimer, the term of this patent is extended or adjusted under 35 U.S.C. 154(b) by 260 days.

(21) Appl. No.: 11/918,533

(22) PCT Filed: Apr. 14, 2006

(86) PCT No.: PCT/IB2006/001418

§ 371 (c)(1),
(2), (4) Date: Jan. 22, 2008

(87) PCT Pub. No.: WO2006/109188

PCT Pub. Date: Oct. 19, 2006

(65) Prior Publication Data

US 2009/0148452 A1 Jun. 11, 2009

(30) Foreign Application Priority Data

Apr. 15, 2005 (EP) .................................. 05290842

(51) Int. Cl.
*A61K 31/70* (2006.01)
*A61K 38/00* (2006.01)
*A61K 48/00* (2006.01)
(52) U.S. Cl. ........................................... 514/12; 514/44
(58) Field of Classification Search ....................... None
See application file for complete search history.

(56) References Cited

U.S. PATENT DOCUMENTS

| 5,580,859 | A | 12/1996 | Felgner et al. | |
|---|---|---|---|---|
| 5,863,796 | A * | 1/1999 | Moore et al. | 435/331 |
| 6,406,693 | B1 | 6/2002 | Thorpe et al. | |
| 6,451,312 | B1 | 9/2002 | Thorpe | |
| 6,638,502 | B1 | 10/2003 | Li et al. | |
| 6,783,760 | B1 | 8/2004 | Thorpe et al. | |
| 6,887,468 | B1 | 5/2005 | Thorpe et al. | |
| 2004/0265273 | A1 | 12/2004 | Li et al. | |

FOREIGN PATENT DOCUMENTS

| EP | 0 386 882 A1 | 9/1990 |
|---|---|---|
| EP | 0 871 459 B1 | 3/2004 |
| EP | 1 222 300 B1 | 5/2006 |
| WO | 91/01330 A1 | 2/1991 |
| WO | 95/03411 A1 | 2/1995 |
| WO | WO 97/12622 A1 | 4/1997 |
| WO | WO 01/27300 A1 | 4/2001 |
| WO | 01/83525 A2 | 11/2001 |
| WO | WO 03/045431 A2 | 6/2003 |
| WO | WO 2004/009131 A1 | 1/2004 |

OTHER PUBLICATIONS

Alberti, L. et al., "A Spliced Isoform of Interleukin 6 mRNA Produced by Renal Cell Carcinoma Encodes for an Interleukin 6 Inhibitor," *Cancer Research*, Jan. 1, 2005, vol. 65, No. 1, pp. 2-5.
Allavena, P. et al., "IL-10 Prevents the Differentiation of Monocytes to Dendritic Cells but Promotes Their Maturation to Macrophages," *Eur. J. Immunol.*, 1998, vol. 28, pp. 359-369.
Almand, B. et al., "Clinical Significance of Defective Dendritic Cell Differentiation in Cancer," *Clinical Cancer Research*, 2000, vol. 6, 1755-1766.
Almand, B. et al., "Increased Production of Immature Myeloid Cells in Cancer Patients: A Mechanism of Immunosuppression in Cancer," *The Journal of Immunolocy*, 2001, vol. 166, pp. 678-689.
Barreda, D.R. et al., "Regulation of Myeloid Development and Function by Colony Stimulating Factors," *Developmental and Comparative Immunology*, 2004, vol. 28, pp. 509-554.
Blin-Wakkach, C, et al. "Hematological Defects in the *oc/oc* Mouse, a Model of Infantile Malignant Osteopetrosis," *Leukemia*, 2004, vol. 18, pp. 1505-1511.
Brigham, K.L. et al., "Rapid Communication: In vivo Transfection of Murine Lungs with a Functioning Prokaryotic Gene Using a Liposome Vehicle," *Am. J. Med. Sci.*, Oct. 1989, vol. 298, No. 4, pp. 278-281.
Bronte, V. et al., "Identification of a $CD11b^+/Gr-1^+/CD31^+$Myeloid Progenitor Capable of Activating or Suppressing $CD8^+T$ Cells," *Blood*, Dec. 1, 2000, vol. 96, No. 12, pp. 3838-3846.
Castaigne, S. et al., "All-Trans Retinoic Acid as a Differentiation Therapy for Acute Promyelocytic Leukemia, I. Clinical Results," *Blood*, Nov. 1, 1990, vol. 76, No. 9, pp. 1704-1709.
Cates, E.C. et al., "Intranasal Exposure of Mice to House Dust Mite Elicits Allergic Airway Inflammation via a GM-CSF-Mediated Mechanism," *The Journal of Immunology*, 2004, vol. 173, pp. 6384-6392.
Corinti, S. et al., "Regulatory Activity of Autocrine IL-10 on Dendritic Cell Functions," *The Journal of Immunology*, 2001, vol. 166, pp. 4312-4318.
De Vries, I.J.M. et al., "Effective Migration of Antigen-Pulsed Dendritic Cells to Lymph Nodes in Melanoma Patients Is Determined by Their Maturation State," *Cancer Research*, Jan. 1, 2003, vol. 63, pp. 12-17.
Dikov, M.M, et al., "Vascular Endothelial Growth Factor Effects on Nuclear Factor-κB Activation in Hematopoietic Progenitor Cells," *Cancer Research*, Mar. 1, 2001, vol. 61, pp. 2015-2021.
Faulkner, L. et al., "Interleukin-10 Does Not Affect Phagocytosis of Particulate Antigen by Bone Marrow-Derived Dendritic Cells but Does Impair Antigen Presentation" *Immunology*, 2000, vol. 99, pp. 523-531.
Feng, J. et al., "The Design of Antagonist Peptide of hIL-6 Based on the Binding Epitope of hIL-6 by Computer-Aided Molecular Modeling," *Peptides*, 2004, vol. 25, pp. 1123-1131.

(Continued)

*Primary Examiner*—Karen A Canella
(74) *Attorney, Agent, or Firm*—DLA Piper LLP (US)

(57) ABSTRACT

A composition is adapted for intra-tumoral administration of a subject suffering from cancer, whereby administration of the composition to the subject induces IMC differentiation by neutralizing a factor implicated in a DC differentiation defect.

5 Claims, 16 Drawing Sheets

OTHER PUBLICATIONS

Gabrilovich, D.I. et al., "Production of Vascular Endothelial Growth Factor by Human Tumors Inhibits the Functional Maturation of Dendritic Cells," *Nature Medicine*, Oct. 1996, vol. 2, No. 10, pp. 1096-1103.

Gabrilovich, D. et al., "Vascular Endothelial Growth Factor Inhibits the Development of Dendritic Cells and Dramatically Affects the Differentiation of Multiple Hematopoietic Lineages In Vivo," *Blood*, Dec. 1, 1998, vol. 92, No. 11, pp. 4150-4166.

Golgher, D. et al., "Depletion of CD25+Regulatory Cells Uncovers Immune Responses to Shared Murine Tumor Rejection Antigens," *Eur. J. Immunol.*, 2002, vol. 32, pp. 3267-3275.

Gri, G. et al., "OX40 Ligand-Transduced Tumor Cell Vaccine Synergizes with GM-CSF and Requires CD4O-Apc Signaling to Boost the Host T Cell Antitumor Response," *The Journal of Immunology*, 2003, vol. 170, pp. 99-106.

Ha, Y. et al., "Role of Granulocyte-Macrophage Colony-Stimulating Factor in Preventing Apoptosis and Improving Functional Outcome in Experimental Spinal Cord Contusion Injury," *J. Neurosurg. Spine*, Jan. 2005, vol. 2, pp. 55-61.

Itoh, M. et al., "Thymus and Autoimmunity: Production of CD25+CD4+Naturally Anergic and Suppressive T Cells as a Key Function of the Thymus in Maintaining Immunologic Self-Tolerance," *The Journal of Immunology*, 1999, vol. 162, pp. 5317-5326.

Jaffe, M.L. et al, "Mechanisms of Tumor-induced Immunosuppression: Evidence for Contact-Dependent T Cell Suppression by Monocytes," *Molecular Medicine*, Nov. 1996, vol. 2., No. 6, pp. 692-701.

Jones, E. et al., "Depletion of CD25+Regulatory Cells Results in Suppression of Melanoma Growth and Induction of Autoreactivity in Mice", *Cancer Immunity*, Feb. 22, 2002, vol. 2, pp. 1-12.

Kusmartsev, S.A. et al., "Gr-1+Myeloid Cells Derived from Tumor-Bearing Mice Inhibit Primary T Cell Activation Induced through CD3/CD28 Costimulation," *The Journal of Immunology*, 2000, vol. 165, pp. 779-785.

Li, R. et al., "Production of Neutralizing Monoclonal Antibody against Human Vascular Endothelial Growth Factor Receptor II," *Acta Pharmacologica Sinica*, Oct. 25, 2004, vol. 25, No. 10, pp. 1292-1298.

Menetrier-Caux, C. et al., "Inhibition of the Differentiation of Dendritic Cells from CD34+ Progenitors by Tumor Cells: Role of Interleukin-6 and Macrophage Colony-Stimulating Factor," *Blood*, Dec. 15, 1998, vol. 92, No. 12, pp. 4778-4791.

Mitani, H. et al.: "Activity of Interleukin 6 in the Differentiation of Monocytes to Macrophages and Dendritic Cells," *British Journal of Haematology*, 2000, vol. 109, pp. 288-295.

Oldenhove' G. et al., "CD4+CD25+ Regulatory T Cells Control T Helper Cell Type 1 Responses to Foreign Antigens Induced by Mature Dendritic Cells In Vivo," *The Journal of Experimental Medicine*, Jul. 21, 2003, vol. 198, No. 2, pp. 259-266.

Onizuka, C, et al., "Tumor Rejection by In Vivo Administration of Anti-CD25 (Interleukin-2 Receptor α) Monoclonal Antibody," *Cancer Research*, Jul. 1, 1999, vol. 59, pp. 3128-3133.

Oyama, T. et al., "Vascular Endothelial Growth Factor Affects Dendritic Cell Maturation through the Inhibition of Nuclear Factor-κB Activation in Hemopoietic Progenitor Cells," *The Journal of Immunology*, 1998, vol. 160, pp. 1224-1232.

Rao, Q. et al., "Membrane-Bound Macrophage Colony-Stimulating Factor Mediated Auto-Juxtacrine Downregulates Matrix Metalloproteinase-9 Release on J6-1 Leukemic Cell," *Experimental Biology and Medicine*, 2004, vol. 229, pp. 946-953.

Reineke, U. et al., "Mapping of the Interleukin-10/Interleukin-10 Receptor Combining Site," *Protein Science*, 1998, vol. 7, 951-960.

Sakaguchi, S. et al., "Immunologic Self-Tolerance Maintained by Activated T Cells Expressing IL-2 Receptor α-Chains (CD25). Breakdown of a Single Mechanism of Self-Tolerance Causes Various Autoimmune Diseases," *The Journal of Immunology*, 1995, vol. 155, pp. 1151-1164.

Sasada, T. et al., "CD4+CD25+ Regulatory T Cells in Patients with Gastrointestinal Malignancies: Possible Involvement of Regulatory T Cells in Disease Progression," *Cancer*, 2003, vol. 98, pp. 1089-1099.

Shurin, G.V. et al., "Neuroblastoma-Derived Gangliosides Inhibit Dendritic Cell Generation and Function." *Cancer Research*, Jan. 1, 2001, vol. 61, pp. 363-369.

Taguchi, O. et al "Administration of Anti-Interleukin-2 Receptor α Antibody in vivo Induces Localized Autoimmune Disease," *Eur. J. Immunol.*, 1996, vol. 26, pp. 1608-1612.

Taverner, T. et al., "Characterization of an Antagonist Interleukin-6 Dimer by Stable Isotope Labeling, Cross-Linking, and Mass Spectrometry," *The Journal of Biological Chemisty*, Nov. 29, 2002, vol. 277, No. 48, pp. 46487-46492.

Toi, M. et al., "Clinical Significance of the Determination of Angiogenic Factors," *European Journal of Cancer*, 1996, vol. 32A, No. 14, pp. 2513-2519.

Wakkach, A. et al., "Characterization of Dendritic Cells that Induce Tolerance and T Regulatory 1 Cell Differentiation In Vivo," *Immunity*, May 2003, vol. 18, pp. 605-617.

Witcher, M. et al., "Combination of Retinoic Acid and Tumor Necrosis Factor Overcomes the Maturation Block in a Variety of Retinoic Acid-Resistant Acute Promyelocytic Leukemia Cells," *Blood*, Nov. 15, 2004, vol. 104, No. 10, pp. 3335-3342.

Woo, E.Y. et al., "Regulatory CD4+ CD25+T Cells in Tumors from Patients with Early-Stage Non-Small Cell Lung Cancer and Late-Stage Ovarian Cancer," *Cancer Research*, Jun. 15, 2001, vol. 61, pp. 4786-4772.

Wu, G.Y. et al., "Receptor-Mediated Gene Delivery and Expression in Vivo," *The Journal of Biological Chemistry*, Oct. 15, 1988, vol. 263, No. 29, pp. 14621-14624.

Xu, D. et al., "CD4+CD25+ Regulatory T Cells Suppress Differentiation and Functions of Th1 and Th2 Cells, *Leishmania major* Infection, and Colitis in Mice", *The Journal of Immunology*, 2003, vol. 170, pp. 394-399.

Yamazaki, S. et al., "Direct Expansion of Functional CD25+CD4+ Regulatory T Cells by Antigen-Processing Dendritic Cells," *The Journal of Experimental Medicine*, Jul. 21, 2003, vol. 198, No. 2, pp. 235-247.

Yang, Z. et al., "A Novel hIL-6 Antagonist Peptide from Computer-Aided Design Contributes to Suppression for Apoptosis in M1 Cells," *Biochemical and Biophysical Research Communications*, 2004, vol. 325, pp. 518-524.

\* cited by examiner

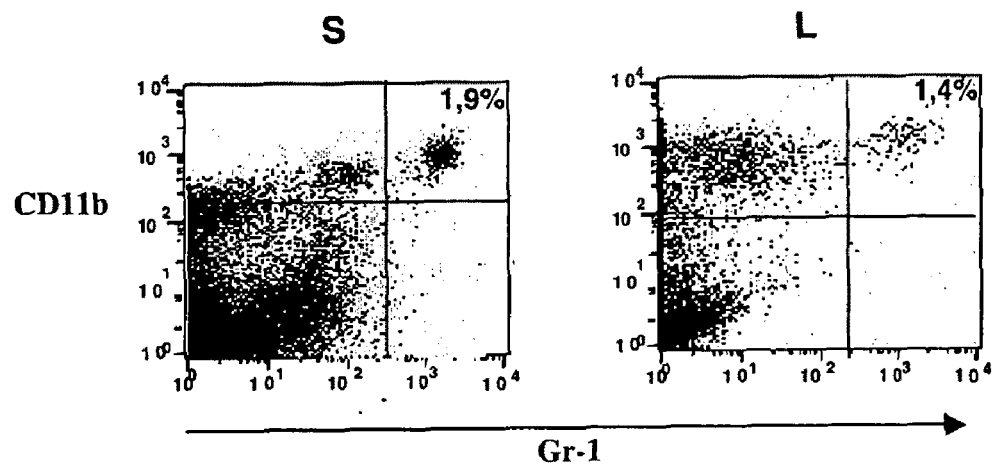
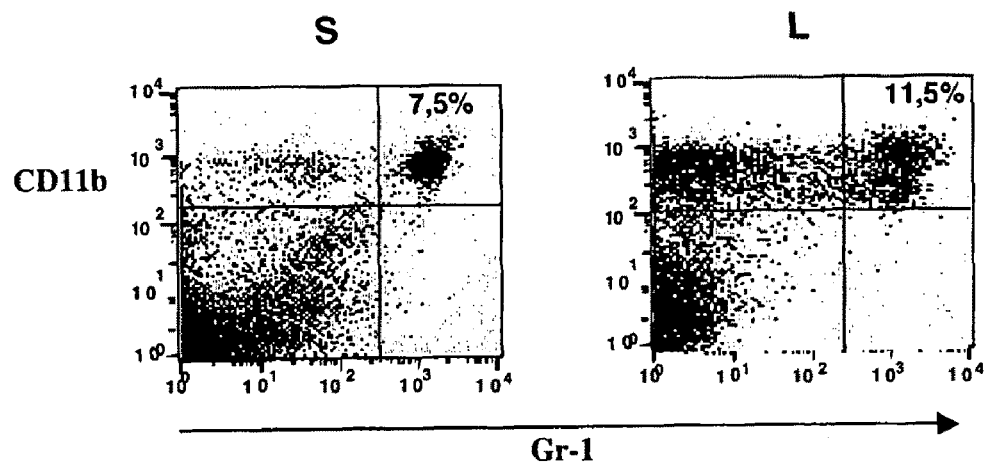
Figure 1

A
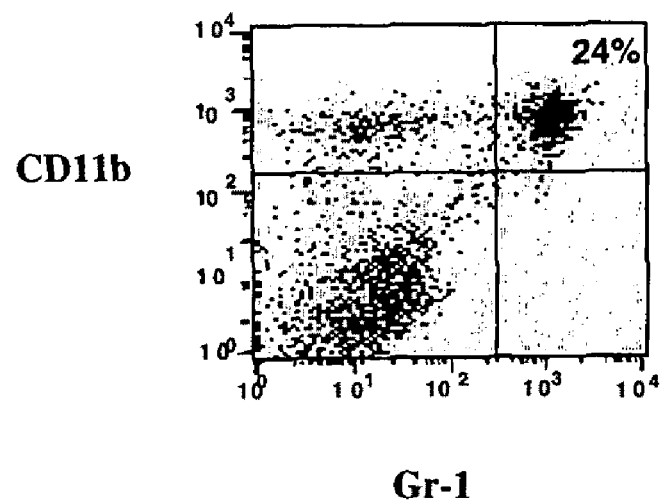
B
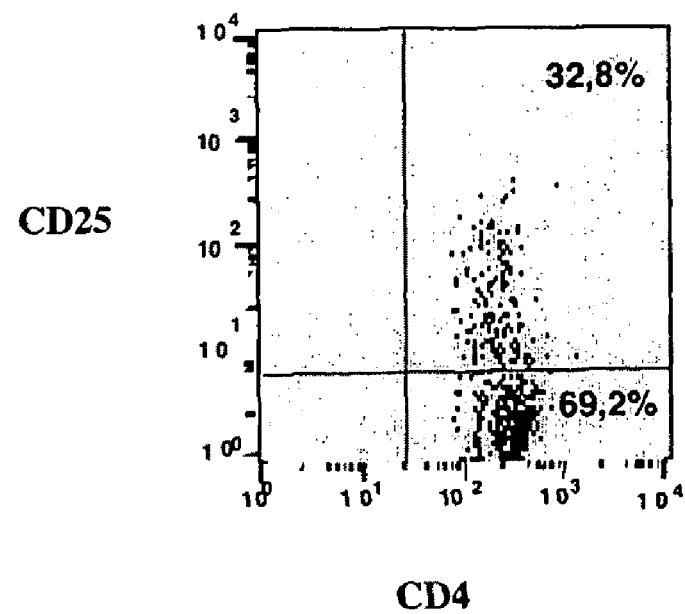
Figure 2

A
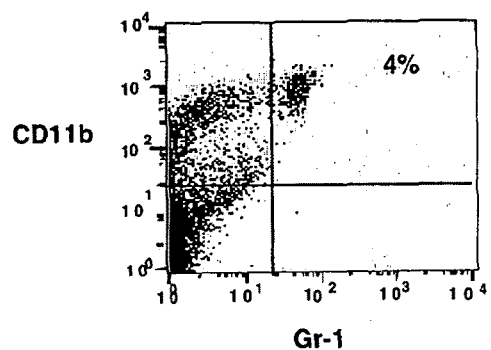
B
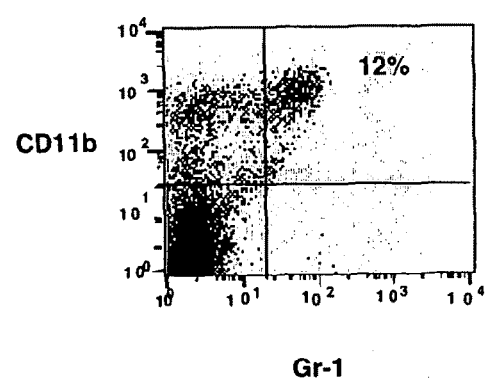
C
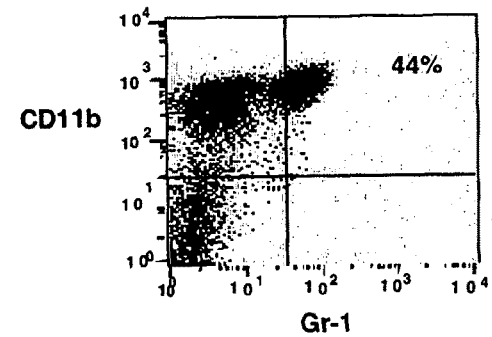
Figure 3

A
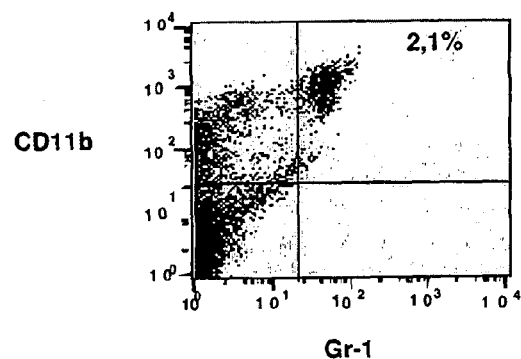
B
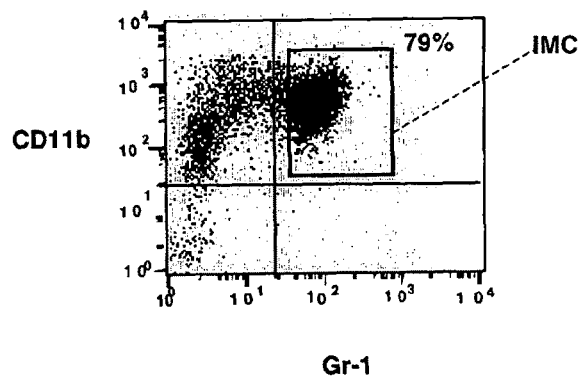
C
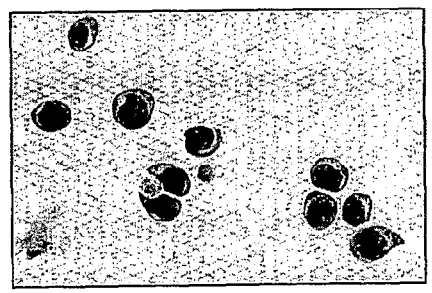
Figure 4

A
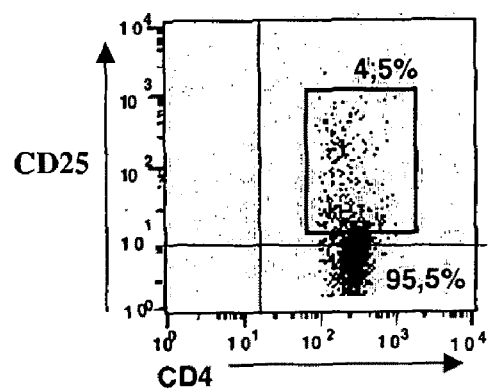
B
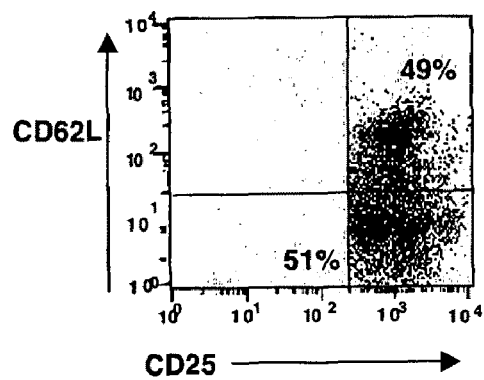
Figure 6

A
B
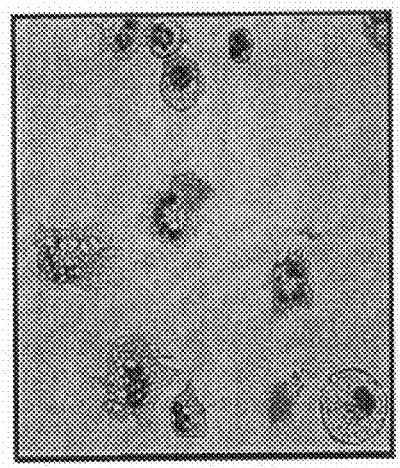
Figure 8

A
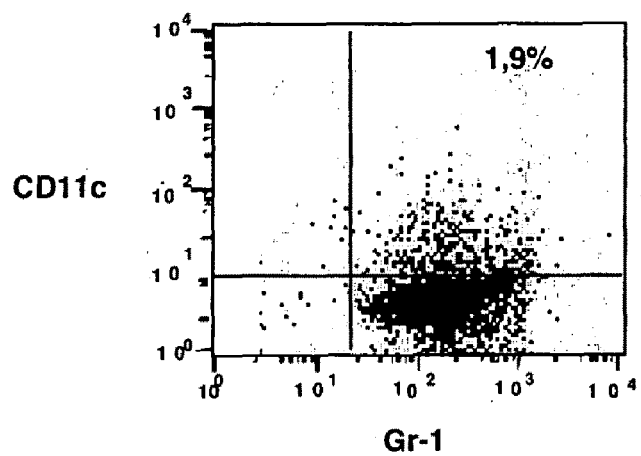
B
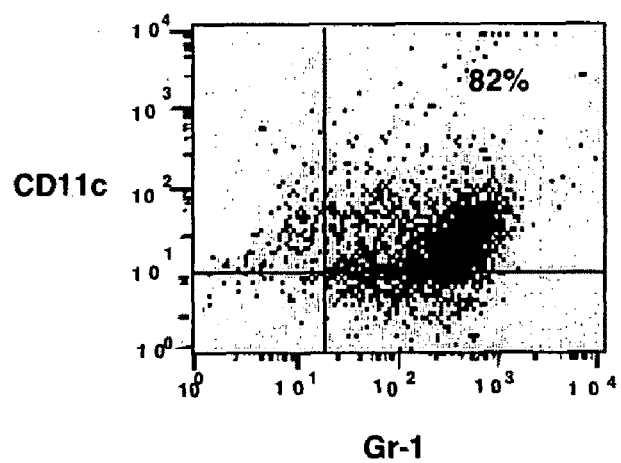
Figure 9

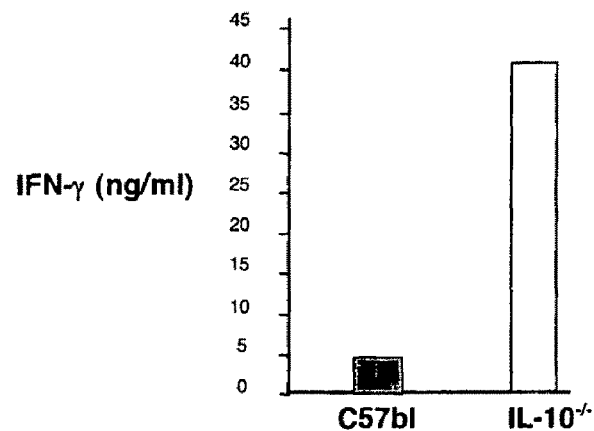
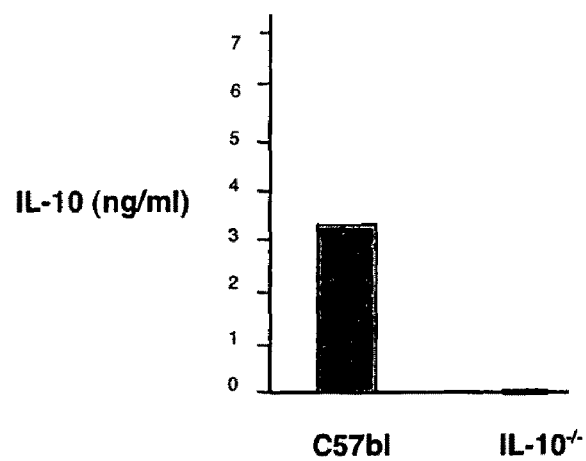
Figure 10

| | | | | | |
|---|---|---|---|---|---|
| CCTGCAGGCG | TTACATAACT | TACGGTAAAT | GGCCCGCCTG | GCTGACCGCC | CAACGACCCC |
| CGCCCATTGA | CGTCAATAAT | GACGTATGTT | CCCATAGTAA | CGCCAATAGG | GACTTTCCAT |
| TGACGTCAAT | GGGTGGAGTA | TTTACGGTAA | ACTGCCCACT | TGGCAGTACA | TCAAGTGTAT |
| CATATGCCAA | GTACGCCCCC | TATTGACGTC | AATGACGGTA | AATGGCCCGC | CTGGCATTAT |
| GCCCAGTACA | TGACCTTATG | GGACTTTCCT | ACTTGGCAGT | ACATCTACGT | ATTAGTCATC |
| GCTATTACCA | TGATGATGCG | GTTTTGGCAG | TACATCAATG | GGCGTGGATA | GCGGTTTGAC |
| TCACGGGGAT | TTCCAAGTCT | CCACCCCATT | GACGTCAATG | GGAGTTTGTT | TTGACTAGTC |
| AGGGCCCCAA | CCCCCCCAAG | CCCCCATTTC | ACAACACGCT | GGCGCTACAG | GCGCGTGACT |
| TCCCCTTGCT | TTGGGGCGGG | GGGCTGAGAC | TCCTATGTGC | TCCGGATTGG | TCAGGCACGG |
| CCTTCGGCCC | CGCCTCCTGC | CACCGCAGAT | TGGCCGCTAG | GCCTCCCCGA | GCGCCCTGCC |
| TCCGAGGGCC | GGCGCACCAT | AAAAGAAGCC | GCCCTAGCCA | CGTCCCCTCG | CAGTTCGGCG |
| GTCCCGCGGG | TCTGTCTCAA | GCTTGCCGCC | AGAACACAGG | TAAGTGCCGT | GTGTGGTTCC |
| CGCGGGCCTG | GCCTCTTTAC | GGGTTATGGC | CCTTGCGTGC | CTTGAATTAC | TTCCATGCCC |
| CTGGCTGCAG | TACGTGATTC | TTGATCCCGA | GCTTCGGGTT | GGAAGTGGGT | GGGAGAGTTC |
| GAGGCCTTGC | GCTTAAGGAG | CCCCTTCGCC | TCGTGCTTGA | GTTGAGGCCT | GGCTTGGGCG |
| CTGGGGCCGC | CGCGTGCTAA | TCTGGTGGCA | CCTTCGCGCC | TGTCTCGCTG | CTTTCGCTAA |
| GTCTCTAGCC | ATTTAAAATT | TTTGATAACC | AGCTGCGACG | CTTTTTTTCT | GGCGAGATAG |
| TCTTGTAAAT | GCGGGCCAAG | ATCTGCACAC | TGGTATTTCG | GTTTTTGGGG | CCGCGGGCGG |
| CGACGGGGCC | CGTGCGTCCC | AGCGCACATG | TTCGGCGAGG | CGGGGCCTGC | GAGCGCGGCC |
| ACCGAGAATC | GGACGGGGGT | AGTCTCAAAC | TGGCCGGCCT | GCTCTGGTGC | CTGGCCTCGC |
| GCCGCCGTGT | ATCGCCCCGC | CCTGGGCGGC | AAGGCTGGCC | CGGTCGGCAC | CAGTTGCGTG |
| AGCGGAAAGA | TGGCCGCTTC | CCGGCCCTGC | TGCAGGGAGC | TCAAAATGGA | GGACGCGGCG |
| CCCGGGAGAG | CGGGCGGGTG | AGTCACCCAC | ACAAAGGAAA | AGGGCCTTTC | CTTCCTCATC |
| CGTCGCTTCA | TGTGACTCCA | CGGAGTACCG | GGCGCCGTCC | AGGCACCTCG | ATTAGTTCTC |
| GAGCTTTTGG | AGTACGTCGT | CTTTAGGTTG | GGGGGAGGGG | TTTTATGCGA | TGGAGTTTCC |
| CCACACTGAG | TGGGTGGAGA | CTGAAGAGTT | AGGCCAGCTT | GGCACTTGAT | GTAATTCTCC |
| TTGGAATTTG | CCCTTTTTGA | GTTTGGATCT | TGCCTCATTC | TCAAGCCTCA | GACAGTGGTT |
| CAAAGTTTTT | TTCTTCCATT | TCAGGTGTCG | TGAAAACTAC | CCCTAAAAGC | CACCATGGAG |
| ACAATGGTTC | TTGCCAGCTC | TACCACCAGC | ATCCACACCA | TGCTGCTCCT | GCTCCTGATG |
| CTCTTCCACC | TGGGACTCCA | AGCTTCAATC | AGTGGCCGGG | ATACCCACCG | TTTAACCAGA |
| ACGTTGAATT | GCAGCTCTAT | TGTCAAGGAG | ATTATAGGGA | AGCTCCCAGA | ACCTGAACTC |
| AAAACTGATG | ATGAAGGACC | CTCTCTGAGG | AATAAGAGCT | TTCGGAGAGT | AAACCTGTCC |
| AAATTCGTGG | AAAGCCAAGG | AGAAGTGGAT | CCTGAGGACA | GATACGTTAT | CAAGTCCAAT |
| CTTCAGAAAC | TTAACTGTTG | CCTGCCTACA | TCTGCGAATG | ACTCTGCGCT | GCCAGGGGTC |
| TTCATTCGAG | ATCTGGATGA | CTTTCGGAAG | AAACTGAGAT | TCTACATGGT | CCACCTTAAC |
| GATCTGGAGA | CAGTGCTAAC | CTCTAGACCA | CCTCAGCCCG | CATCTGGCTC | CGTCTCTCCT |

Figure 11 (1/4)

| | | | | | |
|---|---|---|---|---|---|
| AACCGTGGAA | CCGTGGAATG | TTAAGGATCC | AGAATTCAGA | TATCAGGCTA | GCTGGCCAGA |
| CATGATAAGA | TACATTGATG | AGTTTGGACA | AACCACAACT | AGAATGCAGT | GAAAAAAATG |
| CTTTATTTGT | GAAATTTGTG | ATGCTATTGC | TTTATTTGTA | ACCATTATAA | GCTGCAATAA |
| ACAAGTTAAC | AACAACAATT | GCATTCATTT | TATGTTTCAG | GTTCAGGGGG | AGGTGTGGGA |
| GGTTTTTTAA | AGCAAGTAAA | ACCTCTACAA | ATGTGGTATG | GAAATGTTAA | TTAACTAGCC |
| ATGACCAAAA | TCCCTTAACG | TGAGTTTTCG | TTCCACTGAG | CGTCAGACCC | CGTAGAAAAG |
| ATCAAAGGAT | CTTCTTGAGA | TCCTTTTTTT | CTGCGCGTAA | TCTGCTGCTT | GCAAACAAAA |
| AAACCACCGC | TACCAGCGGT | GGTTTGTTTG | CCGGATCAAG | AGCTACCAAC | TCTTTTTCCG |
| AAGGTAACTG | GCTTCAGCAG | AGCGCAGATA | CCAAATACTG | TTCTTCTAGT | GTAGCCGTAG |
| TTAGGCCACC | ACTTCAAGAA | CTCTGTAGCA | CCGCCTACAT | ACCTCGCTCT | GCTAATCCTG |
| TTACCAGTGG | CTGCTGCCAG | TGGCGATAAG | TCGTGTCTTA | CCGGGTTGGA | CTCAAGACGA |
| TAGTTACCGG | ATAAGGCGCA | GCGGTCGGGC | TGAACGGGGG | GTTCGTGCAC | ACAGCCCAGC |
| TTGGAGCGAA | CGACCTACAC | CGAACTGAGA | TACCTACAGC | GTGAGCTATG | AGAAAGCGCC |
| ACGCTTCCCG | AAGGGAGAAA | GGCGGACAGG | TATCCGGTAA | GCGGCAGGGT | CGGAACAGGA |
| GAGCGCACGA | GGGAGCTTCC | AGGGGGAAAC | GCCTGGTATC | TTTATAGTCC | TGTCGGGTTT |
| CGCCACCTCT | GACTTGAGCG | TCGATTTTTG | TGATGCTCGT | CAGGGGGGCG | GAGCCTATGG |
| AAAAACGCCA | GCAACGCGGC | CTTTTTACGG | TTCCTGGCCT | TTTGCTGGCC | TTTTGCTCAC |
| ATGTTCTTAA | TTAAATTTTT | CAAAAGTAGT | TGACAATTAA | TCATCGGCAT | AGTATATCGG |
| CATAGTATAA | TACGACTCAC | TATAGGAGGG | CCACCATGAA | GAAACCTGAA | CTGACAGCAA |
| CTTCTGTTGA | GAAGTTTCTC | ATTGAAAAAT | TTGATTCTGT | TTCTGATCTC | ATGCAGCTGT |
| CTGAAGGTGA | AGAAAGCAGA | GCCTTTTCTT | TTGATGTTGG | AGGAAGAGGT | TATGTTCTGA |
| GGGTCAATTC | TTGTGCTGAT | GGTTTTTACA | AAGACAGATA | TGTTTACAGA | CACTTTGCCT |
| CTGCTGCTCT | GCCAATTCCA | GAAGTTCTGG | ACATTGGAGA | ATTTTCTGAA | TCTCTCACCT |
| ACTGCATCAG | CAGAAGAGCA | CAAGGAGTCA | CTCTCCAGGA | TCTCCCTGAA | ACTGAGCTGC |
| CAGCTGTTCT | GCAACCTGTT | GCTGAAGCAA | TGGATGCCAT | TGCAGCAGCT | GATCTGAGCC |
| AAACCTCTGG | ATTTGGTCCT | TTTGGTCCCC | AAGGCATTGG | TCAGTACACC | ACTTGGAGGG |
| ATTTCATTTG | TGCCATTGCT | GATCCTCATG | TCTATCACTG | GCAGACTGTG | ATGGATGACA |
| CAGTTTCTGC | TTCTGTTGCT | CAGGCACTGG | ATGAACTCAT | GCTGTGGGCA | GAAGATTGTC |
| CTGAAGTCAG | ACACCTGGTC | CATGCTGATT | TTGGAAGCAA | CAATGTTCTG | ACAGACAATG |
| GCAGAATCAC | TGCAGTCATT | GACTGGTCTG | AAGCCATGTT | TGGAGATTCT | CAATATGAGG |
| TTGCCAACAT | TTTTTTTTGG | AGACCTTGGC | TGGCTTGCAT | GGAACAACAA | ACAAGATATT |
| TTGAAAGAAG | ACACCCAGAA | CTGGCTGGTT | CCCCCAGACT | GAGAGCCTAC | ATGCTCAGAA |
| TTGGCCTGGA | CCAACTGTAT | CAATCTCTGG | TTGATGGAAA | CTTTGATGAT | GCTGCTTGGG |
| CACAAGGAAG | ATGTGATGCC | ATTGTGAGGT | CTGGTGCTGG | AACTGTTGGA | AGAACTCAAA |
| TTGCAAGAAG | GTCTGCTGCT | GTTTGGACTG | ATGGATGTGT | TGAAGTTCTG | GCTGACTCTG |
| GAAACAGGAG | ACCCTCCACA | AGACCCAGAG | CCAAGGAATG | AATATTAGCT | AGGAGTTTCA |

Figure 11 (2/4)

| | | | | | |
|---|---|---|---|---|---|
| GAAAAGGGGG | CCTGAGTGGC | CCCTTTTTTC | AACTTAATTA | ACCTGCAGGG | CCTGAAATAA |
| CCTCTGAAAG | AGGAACTTGG | TTAGGTACCT | TCTGAGGCTG | AAAGAACCAG | CTGTGGAATG |
| TGTGTCAGTT | AGGGTGTGGA | AAGTCCCCAG | GCTCCCCAGC | AGGCAGAAGT | ATGCAAAGCA |
| TGCATCTCAA | TTAGTCAGCA | ACCAGGTGTG | GAAAGTCCCC | AGGCTCCCCA | GCAGGCAGAA |
| GTATGCAAAG | CATGCATCTC | AATTAGTCAG | CAACCATAGT | CCCACTAGTT | CCGCCAGAGC |
| GCGCGAGGGC | CTCCAGCGGC | CGCCCCTCCC | CCACAGCAGG | GGCGGGGTCC | CGCGCCCACC |
| GGAAGGAGCG | GGCTCGGGGC | GGGCGGCGCT | GATTGGCCGG | GGCGGGCCTG | ACGCCGACGC |
| GGCTATAAGA | GACCACAAGC | GACCCGCAGG | GCCAGACGTT | CTTCGCCGAA | GCTTGCCGTC |
| AGAACGCAGG | TGAGGGGCGG | GTGTGGCTTC | CGCGGGCCGC | CGAGCTGGAG | GTCCTGCTCC |
| GAGCGGGCCG | GGCCCCGCTG | TCGTCGGCGG | GGATTAGCTG | CGAGCATTCC | CGCTTCGAGT |
| TGCGGGCGGC | GCGGGAGGCA | GAGTGCGAGG | CCTAGCGGCA | ACCCCGTAGC | CTCGCCTCGT |
| GTCCGGCTTG | AGGCCTAGCG | TGGTGTCCGC | GCCGCCGCCG | CGTGCTACTC | CGGCCGCACT |
| CTGGTCTTTT | TTTTTTTTGT | TGTTGTTGCC | CTGCTGCCTT | CGATTGCCGT | TCAGCAATAG |
| GGGCTAACAA | AGGGAGGGTG | CGGGGCTTGC | TCGCCCGGAG | CCCGGAGAGG | TCATGGTTGG |
| GGAGGAATGG | AGGGACAGGA | GTGGCGGCTG | GGGCCCGCCC | GCCTTCGGAG | CACATGTCCG |
| ACGCCACCTG | GATGGGGCGA | GGCCTGGGGT | TTTTCCCGAA | GCAACCAGGC | TGGGGTTAGC |
| GTGCCGAGGC | CATGTGGCCC | CAGCACCCGG | CACGATCTGG | CTTGGCGGCG | CCGCGTTGCC |
| CTGCCTCCCT | AACTAGGGTG | AGGCCATCCC | GTCCGGCACC | AGTTGCGTGC | GTGGAAAGAT |
| GGCCGCTCCC | GGGCCCTGTT | GCAAGGAGCT | CAAAATGGAG | GACGCGGCAG | CCCGGTGGAG |
| CGGGCGGGTG | AGTCACCCAC | ACAAAGGAAG | AGGGCCTGGT | CCCTCACCGG | CTGCTGCTTC |
| CTGTGACCCC | GTGGTCCTAT | CGGCCGCAAT | AGTCACCTCG | GGCTTTTGAG | CACGGCTAGT |
| CGCGGCGGGG | GGAGGGGATG | TAATGGCGTT | GGAGTTTGTT | CACATTTGGT | GGGTGGAGAC |
| TAGTCAGGCC | AGCCTGGCGC | TGGAAGTCAT | TTTTGGAATT | TGTCCCCTTG | AGTTTTGAGC |
| GGAGCTAATT | CTCGGGCTTC | TTAGCGGTTC | AAAGGTATCT | TTTAAACCCT | TTTTTAGGTG |
| TTGTGAAAAC | CACCGCTAAT | TCAAAGCAAT | CATGAATCTA | GAG<u>ATGTTGT</u> | <u>CGCGTTTGCT</u> |
| <u>CCCATTCCTC</u> | <u>GTCACGATCT</u> | <u>CCAGCCTGAG</u> | <u>CCTAGAATTC</u> | <u>ATTGCATACG</u> | <u>GGACAGAACT</u> |
| <u>GCCAAGCCCT</u> | <u>TCCTATGTGT</u> | <u>GGTTTGAAGC</u> | <u>CAGATTTTC</u> | <u>CAGCACATCC</u> | <u>TCCACTGGAA</u> |
| <u>ACCTATCCCA</u> | <u>AACCAGTCTG</u> | <u>AGAGCACCTA</u> | <u>CTATGAAGTG</u> | <u>GCCCTCAAAC</u> | <u>AGTACGGAAA</u> |
| <u>CTCAACCTGG</u> | <u>AATGACATCC</u> | <u>ATATCTGTAG</u> | <u>AAAGGCTCAG</u> | <u>GCATTGTCCT</u> | <u>GTGATCTCAC</u> |
| <u>AACGTTCACC</u> | <u>CTGGATCTGT</u> | <u>ATCACCGAAG</u> | <u>CTATGGCTAC</u> | <u>CGGGCCAGAG</u> | <u>TCCGGGCAGT</u> |
| <u>GGACAACAGT</u> | <u>CAGTACTCCA</u> | <u>ACTGGACCAC</u> | <u>CACTGAGACT</u> | <u>CGCTTCACAG</u> | <u>TGGATGAAGT</u> |
| <u>GATTCTGACA</u> | <u>GTGGATAGCG</u> | <u>TGACTCTGAA</u> | <u>AGCAATGGAC</u> | <u>GGCATCATCT</u> | <u>ATGGGACAAT</u> |
| <u>CCATCCCCCC</u> | <u>AGGCCCACGA</u> | <u>TAACCCCTGC</u> | <u>AGGGGATGAG</u> | <u>TACGAACAAG</u> | <u>TCTTCAAGGA</u> |
| <u>TCTCCGAGTT</u> | <u>TACAAGATTT</u> | <u>CCATCCGGAA</u> | <u>GTTCTCAGAA</u> | <u>CTAAAGAATG</u> | <u>CAACCAAGAG</u> |
| <u>AGTGAAACAG</u> | <u>GAAACCTTCA</u> | <u>CCCTCACGGT</u> | <u>CCCCATAGGG</u> | <u>GTGAGAAAGT</u> | <u>TTTGTGTCAA</u> |
| <u>GGTGCTGCCC</u> | <u>CGCTTGGAAT</u> | <u>CCCGAATTAA</u> | <u>CAAGGCAGAG</u> | <u>TGGTCGGAGG</u> | <u>AGCAGTGTTT</u> |

Figure 11 (3/4)

| | | | | | |
|---|---|---|---|---|---|
| ACTTATCACG | ACGGAGCAGT | ATTTCACTTA | GCCTAGGATT | ATCCCTAATA | CCTGCCACCC |
| CACTCTTAAT | CAGTGGTGGA | AGAACGGTCT | CAGAACTGTT | TGTTTCAATT | GGCCATTTAA |
| GTTTAGTAGT | AAAAGACTGG | TTAATGATAA | CAATGCATCG | TAAAACCTTC | AGAAGGAAAG |
| GAGAATGTTT | TGTGGACCAC | TTTGGTTTTC | TTTTTTGCGT | GTGGCAGTTT | TAAGTTATTA |
| GTTTTAAAA | TCAGTACTTT | TTAATGGAAA | CAACTTGACC | AAAAATTTGT | CACAGAATTT |
| TGAGACCCAT | TAAAAAAGTT | AAATGAGAAA | CCTGTGTGTT | CCTTTGGTCA | ACACCGAGAC |
| ATTTAGGTGA | AAGACATCTA | ATTCTGGTTT | TACGAATCTG | GAAACTTCTT | GAAAATGTAA |
| TTCTTGAGTT | AACACTTCTG | GGTGGAGAAT | AGGGTTGTTT | TCCCCCCACA | TAATTGGAAG |
| GGGAAGGAAT | ATCATTTAAA | GCTATGGGAG | GGTTGCTTTG | ATTACAACAC | TGGAGAGAAA |
| TGCAGCATGT | TGCTGATTGC | CTGTCACTAA | AACAGGCCAA | AAACTGAGTC | CTTGGGTTGC |
| ATAGAAAGCT | G | | | | |

Figure 11 (4/4)

SEQUENCE LISTING

<160> NUMBER OF SEQ ID NOS: 9

<210> SEQ ID NO 1
<211> LENGTH: 7091
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

-continued

```
cctgcaggcg ttacataact tacggtaaat ggcccgcctg gctgaccgcc caacgacccc      60
cgcccattga cgtcaataat gacgtatgtt cccatagtaa cgccaatagg gactttccat     120
tgacgtcaat gggtggagta tttacggtaa actgcccact tggcagtaca tcaagtgtat     180
catatgccaa gtacgccccc tattgacgtc aatgacggta aatggcccgc ctggcattat     240
gcccagtaca tgaccttatg gactttcct acttggcagt acatctacgt attagtcatc      300
gctattacca tgatgatgcg gttttggcag tacatcaatg ggcgtggata gcggtttgac     360
tcacggggat ttccaagtct ccaccccatt gacgtcaatg ggagtttgtt ttgactagtc     420
agggcccaa cccccaaag ccccattc acaacacgct ggcgctacag gcgcgtgact        480
tcccttgct ttggggcggg gggctgagac tcctatgtgc tccggattgg tcaggcacgg      540
ccttcggccc cgcctcctgc caccgcagat tggccgctag gctccccga cgccctgcc      600
tccgagggcc ggcgcaccat aaaagaagcc gccctagcca cgtcccctcg cagttcggcg    660
gtcccgcggg tctgtctcaa gcttgccgcc agaacacagg taagtgccgt gtgtggttcc   720
cgcgggcctg gcctctttac gggttatggc ccttgcgtgc cttgaattac ttccatgccc   780
ctggctgcag tacgtgattc ttgatcccga gcttcgggtt ggaagtgggt gggagagttc   840
gaggccttgc gcttaaggag ccccttcgcc tcgtgcttga gttgaggcct ggcttgggcg    900
ctggggccgc cgcgtgctaa tctggtggca ccttcgcgcc tgtctcgctg ctttcgctaa    960
gtctctagcc atttaaaatt tttgataacc agctgcgacg ctttttttct ggcgagatag   1020
tcttgtaaat gcgggccaag atctgcacac tggtatttcg gttttgggg ccgcgggcgg    1080
cgacggggcc cgtgcgtccc agcgcacatg ttcggcgagg cggggcctgc gagcgcggcc   1140
accgagaatc ggacgggggt agtctcaaac tggccggcct gctctggtgc ctggcctcgc   1200
gccgccgtgt atcgccccgc cctgggcggc aaggctggcc cggtcggcac cagttgcgtg   1260
agcggaaaga tggccgcttc ccggccctgc tgcagggagc tcaaaatgga ggacgcggcg   1320
cccgggagag cgggcgggtg agtcacccac acaaaggaaa agggcctttc cttcctcatc   1380
cgtcgcttca tgtgactcca cggagtaccg gcgccgtcc aggcacctcg attagttctc    1440
gagcttttgg agtacgtcgt ctttaggttg ggggagggg ttttatgcga tggagtttcc    1500
ccacactgag tgggtggaga ctgaagagtt aggccagctt ggcacttgat gtaattctcc   1560
ttggaatttg ccctttttga gtttggatct tgcctcattc tcaagcctca gacagtggtt   1620
caaagttttt ttcttccatt tcaggtgtcg tgaaaactac ccctaaaagc caccatggag   1680
acaatggttc ttgccagctc taccaccagc atccaccaca tgctgctcct gctcctgatg   1740
ctcttccacc tgggactcca agcttcaatg agtggccggg atacccaccg tttaaccaga   1800
acgttgaatt gcagctctat tgtcaaggag attatagggga agctcccaga acctgaactc   1860
aaaactgatg atgaaggacc ctctctgagg aataagagct ttcggagagt aaacctgtcc   1920
aaattcgtgg aaagccaagg agaagtggat cctgaggaca gatacgttat caagtccaat   1980
cttcagaaac ttaactgttg cctgcctaca tctgcgaatg actctgcgct gccagggggtc   2040
ttcattcgag atctggatga ctttcggaag aaactgagat tctacatggt ccaccttaac   2100
gatctggaga cagtgctaac ctctagacca cctcagcccg catctggctc cgtctctcct   2160
aaccgtggaa ccgtggaatg ttaaggatcc agaattcaga tatcaggcta gctgccaga    2220
catgataaga tacattgatg agtttggaca aaccacaact agaatgcagt gaaaaaaatg   2280
ctttatttgt gaaatttgtg atgctattgc tttatttgta accattataa gctgcaataa   2340
acaagttaac aacaacaatt gcattcattt tatgtttcag gttcaggggg aggtgtggga   2400
```

```
ggtttttaa agcaagtaaa acctctacaa atgtggtatg gaaatgttaa ttaactagcc   2460
atgaccaaaa tcccttaacg tgagttttcg ttccactgag cgtcagaccc cgtagaaaag   2520
atcaaaggat cttcttgaga tcctttttt ctgcgcgtaa tctgctgctt gcaaacaaaa    2580
aaaccaccgc taccagcggt ggtttgtttg ccggatcaag agctaccaac tcttttccg    2640
aaggtaactg gcttcagcag agcgcagata ccaaatactg ttcttctagt gtagccgtag   2700
ttaggccacc acttcaagaa ctctgtagca ccgcctacat acctcgctct gctaatcctg   2760
ttaccagtgg ctgctgccag tggcgataag tcgtgtctta ccgggttgga ctcaagacga   2820
tagttaccgg ataaggcgca gcggtcgggc tgaacggggg gttcgtgcac acagcccagc   2880
ttggagcgaa cgacctacac cgaactgaga tacctacagc gtgagctatg agaaagcgcc   2940
acgcttcccg aagggagaaa ggcggacagg tatccggtaa gcggcagggt cggaacagga   3000
gagcgcacga gggagcttcc aggggggaaac gcctggtatc tttatagtcc tgtcgggttt   3060
cgccacctct gacttgagcg tcgatttttg tgatgctcgt caggggggcg agcctatgg    3120
aaaaacgcca gcaacgcggc cttttttacg ttcctggcct tttgctggcc ttttgctcac   3180
atgttcttaa ttaaatttt caaaagtagt tgacaattaa tcatcggcat agtatatcgg    3240
catagtataa tacgactcac tataggaggg ccaccatgaa gaaacctgaa ctgacagcaa   3300
cttctgttga gaagtttctc attgaaaaat ttgattctgt ttctgatctc atgcagctgt   3360
ctgaaggtga agaaagcaga gccttttctt ttgatgttgg aggaagaggt tatgttctga   3420
gggtcaattc ttgtgctgat ggttttaca aagacagata tgtttacaga cactttgcct    3480
ctgctgctct gccaattcca gaagttctgg acattggaga attttctgaa tctctcacct   3540
actgcatcag cagaagagca caaggagtca ctctccagga tctccctgaa actgagctgc   3600
cagctgttct gcaacctgtt gctgaagcaa tggatgccat tgcagcagct gatctgagcc   3660
aaacctctgg atttggtcct tttggtcccc aaggcattgg tcagtacacc acttggaggg   3720
atttcatttg tgccattgct gatcctcatg tctatcactg gcagactgtg atggatgaca   3780
cagtttctgc ttctgttgct caggcactgg atgaactcat gctgtgggca gaagattgtc   3840
ctgaagtcag acacctggtc catgctgatt ttggaagcaa caatgttctg acagacaatg   3900
gcagaatcac tgcagtcatt gactggtctg aagccatgtt tggagattct caatatgagg   3960
ttgccaacat tttttttgg agaccttggc tggcttgcat ggaacaacaa acaagatatt    4020
ttgaaagaag acacccagaa ctggctggtt cccccagact gagagcctac atgctcagaa   4080
ttggcctgga ccaactgtat caatctctgg ttgatggaaa ctttgatgat gctgcttggg   4140
cacaaggaag atgtgatgcc attgtgaggt ctggtgctgg aactgttgga agaactcaaa   4200
ttgcaagaag gtctgctgct gtttggactg atggatgtgt tgaagttctg gctgactctg   4260
gaaacaggag accctccaca agacccagag ccaaggaatg aatattagct aggagtttca   4320
gaaaagggg cctgagtggc cccttttttc aacttaatta acctgcaggg cctgaaataa   4380
cctctgaaag aggaacttgg ttaggtacct tctgaggctg aaagaaccag ctgtggaatg   4440
tgtgtcagtt agggtgtgga aagtccccag gctccccagc aggcagaagt atgcaaagca   4500
tgcatctcaa ttagtcagca accaggtgtg gaaagtcccc aggctcccca gcaggcagaa   4560
gtatgcaaag catgcatctc aattagtcag caaccatagt cccactagtt ccgccagagc   4620
gcgcgagggc ctccagcggc cgcccctccc ccacagcagg gcggggtcc cgcgcccacc    4680
ggaaggagcg ggctcggggc gggcggcgct gattggccgg ggcgggcctg acgccgacgc   4740
```

-continued

```
ggctataaga gaccacaagc gacccgcagg gccagacgtt cttcgccgaa gcttgccgtc    4800
agaacgcagg tgaggggcgg gtgtggcttc cgcgggccgc cgagctggag gtcctgctcc    4860
gagcgggccg ggccccgctg tcgtcggcgg ggattagctg cgagcattcc cgcttcgagt    4920
tgcgggcggc gcggaggca gagtgcgagg cctagcggca accccgtagc ctcgcctcgt     4980
gtccggcttg aggcctagcg tggtgtccgc gccgccgccg cgtgctactc cggccgcact    5040
ctggtctttt ttttttttgt tgttgttgcc ctgctgcctt cgattgccgt tcagcaatag    5100
gggctaacaa agggagggtg cggggcttgc tcgcccggag cccggagagg tcatggttgg    5160
ggaggaatga agggacagga gtggcggctg gggcccgccc gccttcggag cacatgtccg    5220
acgccacctg gatggggcga ggcctggggt ttttcccgaa gcaaccaggc tggggttagc    5280
gtgccgaggc catgtggccc cagcacccgg cacgatctgg cttggcggcg ccgcgttgcc    5340
ctgcctccct aactagggtg aggccatccc gtccggcacc agttgcgtgc gtggaaagat    5400
ggccgctccc gggcccgtt gcaaggagct caaaatggag gacgcggcag cccggtggag     5460
cgggcgggtg agtcacccac acaaaggaag agggcctggt ccctcaccgg ctgctgcttc    5520
ctgtgacccc gtggtcctat cggccgcaat agtcacctcg gcttttgag cacggctagt     5580
cgcggcgggg ggaggggatg taatggcgtt ggagtttgtt cacatttggt gggtggagac    5640
tagtcaggcc agcctggcgc tggaagtcat ttttggaatt tgtccccttg agttttgagc    5700
ggagctaatt ctcgggcttc ttagcggttc aaaggtatct tttaaaccct tttttaggtg    5760
ttgtgaaaac caccgctaat tcaaagcaat catgaatcta gagatgttgt cgcgtttgct    5820
cccattcctc gtcacgatct ccagcctgag cctagaattc attgcatacg ggacagaact    5880
gccaagccct tcctatgtgt ggtttgaagc cagatttttc cagcacatcc tccactggaa    5940
acctatccca aaccagtctg agagcaccta ctatgaagtg gccctcaaac agtacggaaa    6000
ctcaacctgg aatgacatcc atatctgtag aaaggctcag gcattgtcct gtgatctcac    6060
aacgttcacc ctggatctgt atcaccgaag ctatggctac cgggccagag tccgggcagt    6120
ggacaacagt cagtactcca actgaccac cactgagact cgcttcacag tggatgaagt     6180
gattctgaca gtggatagcg tgactctgaa agcaatggac ggcatcatct atgggacaat    6240
ccatccccc aggcccacga taaccctgc aggggatgag tacgaacaag tcttcaagga      6300
tctccgagtt tacaagattt ccatccggaa gttctcagaa ctaaagaatg caaccaagag    6360
agtgaaacag gaaaccttca ccctcacggt cccataggg gtgagaaagt tttgtgtcaa     6420
ggtgctgccc cgcttggaat cccgaattaa caaggcagag tggtcggagg agcagtgttt    6480
acttatcacg acggagcagt atttcactta gcctaggatt atccctaata cctgccaccc    6540
cactcttaat cagtggtgga agaacggtct cagaactgtt tgtttcaatt ggccatttaa    6600
gtttagtagt aaaagactgg ttaatgataa caatgcatcg taaaaccttc agaaggaaag    6660
gagaatgttt tgtggaccac tttggttttc tttttttgcgt gtggcagttt taagttatta    6720
gtttttaaaa tcagtacttt ttaatggaaa caacttgacc aaaaatttgt cacagaattt    6780
tgagacccat taaaaaagtt aaatgagaaa cctgtgtgtt cctttggtca acaccgagac    6840
atttaggtga agacatctca attctggttt tacgaatctg gaaacttctt gaaaatgtaa    6900
ttcttgagtt aacacttctg ggtggagaat agggttgttt tcccccacac taattggaag    6960
gggaaggaat atcatttaaa gctatgggag ggttgctttg attacaacac tggagagaaa    7020
tgcagcatgt tgctgattgc ctgtcactaa aacaggccaa aaactgagtc cttgggttgc    7080
atagaaagct g                                                        7091
```

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Ile Ser Gln Ala Val His Ala Ala His Ala Glu Ile Asn Glu Ala Gly
 1               5                  10                  15

Arg

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
tccatgacgt tcctgacgtt                                                   20

<210> SEQ ID NO 4
<211> LENGTH: 274
<212> TYPE: PRT
<213> ORGANISM: Mus musculus

<400> SEQUENCE: 4

Leu Ser Arg Leu Leu Pro Phe Leu Val Thr Ile Ser Ser Leu Ser Leu
 1               5                  10                  15

Glu Phe Ile Ala Tyr Gly Thr Glu Leu Pro Ser Pro Ser Tyr Val Trp
            20                  25                  30

Phe Glu Ala Arg Phe Phe Gln His Ile Leu His Trp Lys Pro Ile Pro
        35                  40                  45

Asn Gln Ser Glu Ser Thr Tyr Tyr Glu Val Ala Leu Lys Gln Tyr Gly
    50                  55                  60

Asn Ser Thr Trp Asn Asp Ile His Ile Cys Arg Lys Ala Gln Ala Leu
65                  70                  75                  80

Ser Cys Asp Leu Thr Thr Phe Thr Leu Asp Leu Tyr His Arg Ser Tyr
                85                  90                  95

Gly Tyr Arg Ala Arg Val Arg Ala Val Asp Asn Ser Gln Tyr Ser Asn
            100                 105                 110

Trp Thr Thr Thr Glu Thr Arg Phe Thr Val Asp Glu Val Ile Leu Thr
        115                 120                 125

Val Asp Ser Val Thr Leu Lys Ala Met Asp Gly Ile Ile Tyr Gly Thr
    130                 135                 140

Ile His Pro Pro Arg Pro Thr Ile Thr Pro Ala Gly Asp Glu Tyr Glu
145                 150                 155                 160

Gln Val Phe Lys Asp Leu Arg Val Tyr Lys Ile Ser Ile Arg Lys Phe
                165                 170                 175

Ser Glu Leu Lys Asn Ala Thr Lys Arg Val Lys Gln Glu Thr Phe Thr
            180                 185                 190

Leu Thr Val Pro Ile Gly Val Arg Lys Phe Cys Val Lys Val Leu Pro
        195                 200                 205

Arg Leu Glu Ser Arg Ile Asn Lys Ala Glu Trp Ser Glu Glu Gln Cys
    210                 215                 220

```
Leu Leu Ile Thr Thr Glu Gln Tyr Phe Thr Val Thr Asn Leu Ser Ile
225                 230                 235                 240

Leu Val Ile Ser Met Leu Leu Phe Cys Gly Ile Leu Val Cys Leu Val
            245                 250                 255

Leu Gln Trp Tyr Ile Arg His Pro Gly Lys Leu Pro Thr Val Leu Val
        260                 265                 270

Phe Lys

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tctagagatg ttgtcgcgtt tgctcc                                              26

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctaggctaa gtgaaatact gctccgtcg                                           29

<210> SEQ ID NO 7
<211> LENGTH: 166
<212> TYPE: PRT
<213> ORGANISM: Mus musculus

<400> SEQUENCE: 7

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Gly Arg
            20                  25                  30

Asp Thr His Arg Leu Thr Arg Thr Leu Asn Cys Ser Ser Ile Val Lys
        35                  40                  45

Glu Ile Ile Gly Lys Leu Pro Glu Pro Glu Leu Lys Thr Asp Asp Glu
    50                  55                  60

Gly Pro Ser Leu Arg Asn Lys Ser Phe Arg Arg Val Asn Leu Ser Lys
65                  70                  75                  80

Phe Val Glu Ser Gln Gly Glu Val Asp Pro Glu Asp Arg Tyr Val Ile
                85                  90                  95

Lys Ser Asn Leu Gln Lys Leu Asn Cys Cys Leu Pro Thr Ser Ala Asn
            100                 105                 110

Asp Ser Ala Leu Pro Gly Val Phe Ile Arg Asp Leu Asp Asp Phe Arg
        115                 120                 125

Lys Lys Leu Arg Phe Tyr Met Val His Leu Asn Asp Leu Glu Thr Val
130                 135                 140

Leu Thr Ser Arg Pro Pro Gln Pro Ala Ser Gly Ser Val Ser Pro Asn
145                 150                 155                 160

Arg Gly Thr Val Glu Cys
                165
```

```
<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatggagac aatggttctt gccagc                                          26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggatccttaa cattccacgg ttccacg                                         27
```

COMPOSITION FOR TREATING CANCER ADAPTED FOR INTRA-TUMORAL ADMINISTRATION AND USES THEREOF

RELATED APPLICATION

This is a §371 of International Application No. PCT/IB2006/001418, with an international filing date of Apr. 14, 2006 (WO 2006/109188 A2, published Oct. 19, 2006), which is based on European Patent Application No. 05290842.3, filed Apr. 15, 2005.

TECHNICAL FIELD

This disclosure relates to a composition for treating cancer and uses thereof.

BACKGROUND

Failure of T cells from tumor-bearing hosts to effectively recognize and eliminate tumor cells is one of the major factors of tumor escape from immune system control. An effective antitumor immune response requires participation of the host bone marrow antigen-presenting cell (APC) responsible for the presentation of tumor-specific antigens. Dendritic cells (DC) and macrophages are the two most potent groups of APC. These cells are capable of inducing primary immune responses including the cytotoxic T-lymphocyte response.

Recent studies have clearly demonstrated that the immunostimulatory characteristics of DC are dependent on their maturation state. Increasing evidence supports the notion that both immune activation and immune suppression depend on antigen presentation by APC.

DC as well as macrophages and granulocytes arise from a common myeloid progenitor that has the ability to capture antigen but lacks the expression of major histocompatibility complex (MHC) class II and co-stimulatory molecules. Mature DC loaded with antigen are highly effective in eliciting a protective immune response against tumors, whereas immature DC may induce the antigen specific inhibition of CD8+ T cell effector function.

It appears that impaired balance between mature and immature myeloid cells is one of the hallmarks of cancer. There is increasing evidence that progressive tumor growth is associated with an accumulation of immature myeloid cells, monocytes/macrophages, and with a decreased number and function of DC in cancer patients as well as in tumor-bearing mice. The increased presence of immature myeloid cells (IMCs) capable of inhibiting T cells responses could be the major factor responsible for immune suppression in cancer patient.

The growth of many mouse carcinomas is associated with the early development of splenomegaly and the marked accumulation of IMC in the lymphoid organs (JAFFE et al., *Mol. Med.*, vol. 2, p: 692-701, 1996; KUSMARTSEV et al., *J. Immunol.*, vol. 165, p: 779-85, 2000). Decreased presence of DC in the peripheral blood of patients with breast, lung, head and neck cancer was associated with the accumulation in the peripheral blood of cells lacking markers specific for mature myeloid and lymphoid lineages (ALMAND et al., *Clin. Cancer Res.*, vol. 6, 1755-1766, 2000). About one third of these cells were immature macrophages and DC and the remaining cells were IMC at earlier stages of differentiation (ALMAND et al., *J. Immunol.*, vol. 166, 678-689, 2001). The peripheral blood presence of these cells was dramatically increased in patients with advanced stage cancer, but dropped considerably within three to four weeks after surgical resection of the tumor. This finding is consistent with the hypothesis that the generation of IMC is due to the production of soluble factors by tumors.

Consistent with this hypothesis, it has been shown that several tumor-derived factors affect DC maturation from hematopoietic progenitor cells (HPC).

VEGF is produced by most tumors, and its production is closely associated with poor prognosis (TOI et al., *Eur. J. Cancer*, vol. 32A, p: 2513-9, 1996). It has been shown that neutralizing anti-VEGF antibody blocked the negative effects of tumour cell supernatants on DC maturation in vitro (GABRILOVICH et al., *Nat. Med.*, vol. 2, p: 1096-103, 1996). Moreover, a continuous in vivo VEGF infusion results in a dramatic inhibition of DC production (GABRILOVICH et al., *Blood*, vol. 92, p: 4150-4166, 1998).

VEGF inhibits the activation of transcription factor NF-κB in hematopoietic progenitor cells, which is accompanied by alterations in the development of multiple lineages of hematopoietic cells (DIKOV et al., *Cancer Res.*, vol. 61, p: 2015-21, 2001). Chronic administration of recombinant VEGF in naïve mice results in an inhibition of DC development and in an increased production of B cells and immature GR-1+ myeloid cells (OYAMA et al., *J. Immunol.*, vol. 160, p: 1224-32, 1998).

GM-CSF is another factor that has been shown to be responsible for the stimulation of myelopoiesis in tumor-bearing host. The chronic administration of GM-CSF to mice results in the generation of a cell population that morphologically resembles granulocyte-monocyte progenitors that express the granulocyte-monocyte markers Mac-1 and Gr-1 (BRONTE et al., *Blood*, vol. 96, p: 3838-46, 2000).

Other tumor-derived factors such as M-CSF, IL-6 (MENETRIER-CAUX et al., *Blood*, vol. 92, p: 4778-4791, 1998), and IL-10 (ALLAVENA et al., *Eur. J. Immunol.*, vol. 28, p: 359-69, 1998; FAULKNER et al., *Immunology*, vol. 99, p: 523-31, 2000) or gangliosides (SHURIN et al., *Cancer Res.*, vol. 61, p: 363-9, 2001) have also been involved in defective DC differentiation in vitro. Neutralizing anti-IL-6 and anti-M-CSF antibodies abrogate the negative effect of supernatants from renal cell carcinomas on DC differentiation (MENETRIER-CAUX et al., above-mentioned, 1998). However, it appears that these factors do not stimulate myelopoiesis and mostly affect relatively mature cells. Moreover, IL-10 appears to prevent the differentiation of monocytes to DC, but promotes their maturation to macrophages (ALLA-VENA et al., above-mentioned, 1998). Furthermore, ALMAND et al. (2000, above-mentioned) has shown that only patients with peripheral blood elevated levels of VEGF showed statistically significant increased of IMCs after measuring the levels of M-CSF, GM-CSF, IL-6, IL-10, TGF-β, and VEGF.

The characterization of IMCs has shown that these cells actively suppress Ag-specific T cells responses and contributes to tumor nonresponsiveness (ALMAND et al., above-mentioned, 2001). Thus, IMCs actively inhibit CD8+ T cell effector function, MHC class-II associated T-specific proliferation and MHC class I-restricted IFN-γ production in the presence of functionally competent DC. It has been suggested that physiologically, IMCs may serve as a defense mechanism that limits the expansion of activated T cells and prevents the development of autoimmune diseases. However, in the case of cancer, the accumulation of IMCs may lead to the profound suppression of immune responses.

Consequently, IMCs depletion or differentiation constitutes actually an important strategy to improve immune response in cancer.

Different ways of therapies have been explored by in vitro IMCs differentiation experiments. Thus, it has been shown that a combination of ATRA and GM-CSF is able to induce the differentiation of the majority of IMCs into relatively mature DC (ALMAND et al., above-mentioned, 2001). ATRA is a naturally occurring isomer of retinoic acid that is successfully used in differentiation induction therapy in patients with acute promyelotic leukaemia (CASTAIGNE et al., Blood, vol. 76, p: 1704-9, 1990).

However, if the general in vivo induction of the differentiation of IMCs by an adapted factor could induce a tumor remission, it could also induce the development of an autoimmune response.

It could therefore be advantageous to provide a composition for inducing IMCs differentiation within the tumor sites to induce tumor remission without any side effects.

SUMMARY

We provide a method of treating cancer including intratumorally administering a therapeutically effective amount of a composition including a (i) protein able to neutralize the binding of IL-10 to its receptor, or (ii) a nucleic acid encoding for the protein (i), or (iii) a cell transformed by the vector (ii) and expressing the protein (iii), to a patient.

BRIEF DESCRIPTION OF THE DRAWINGS

FIGS. 1A and 1B represent the expression pattern of CD11b and Gr-1 in mononuclear purified cells from spleens and livers of normal and C26 mice, respectively.

FIGS. 2A and 2B represent the expression patterns of CD11b and Gr-1 in mononuclear cells from tumors of C26 mice and CD25 and CD4 in T cells from tumors from C26 mice, respectively.

FIGS. 3A, 3B and 3C represent the expression patterns of CD11b and Gr-1 in mononuclear cells from spleens of normal and C26 33-week-old mice and CD11b and Gr-1 in mononuclear cells from tumors of C26 33-week-old mice, respectively.

FIGS. 4A and B represent the expression pattern of CD11b and Gr-1 in mononuclear cells immediately after purification and after twelve days of culture, respectively, from spleens of normal mice.

FIG. 4C shows the morphology of amplified IMC after twelve days of culture by GIEMSA coloration.

FIG. 6A represents the expression of CD24 and CD25 by the spleen cells of homozygous DO11.10. FIG. 6B represents the expression of CD62L and CD25 after three days of culturing.

FIGS. 8A and 8B show the morphology of cells after twelve days of culture by GIEMSA coloration.

FIGS. 9A and 9B represent the expression pattern of CD11c and Gr-1 in amplified IMC cells from spleens of normal and C26 mice at the end of twelve days with or without anti-IL-10R antibody and CpG dinucleotides.

FIGS. 10A and 10B graphically represent the expression of IFN-γ and IL-10 by naïve CD4+ cells cultured under different conditions.

FIG. 11 shows p310R sequence wherein IL-10 and IL-3 sequences are underlined and in bold, respectively.

DETAILED DESCRIPTION

Figure 5:
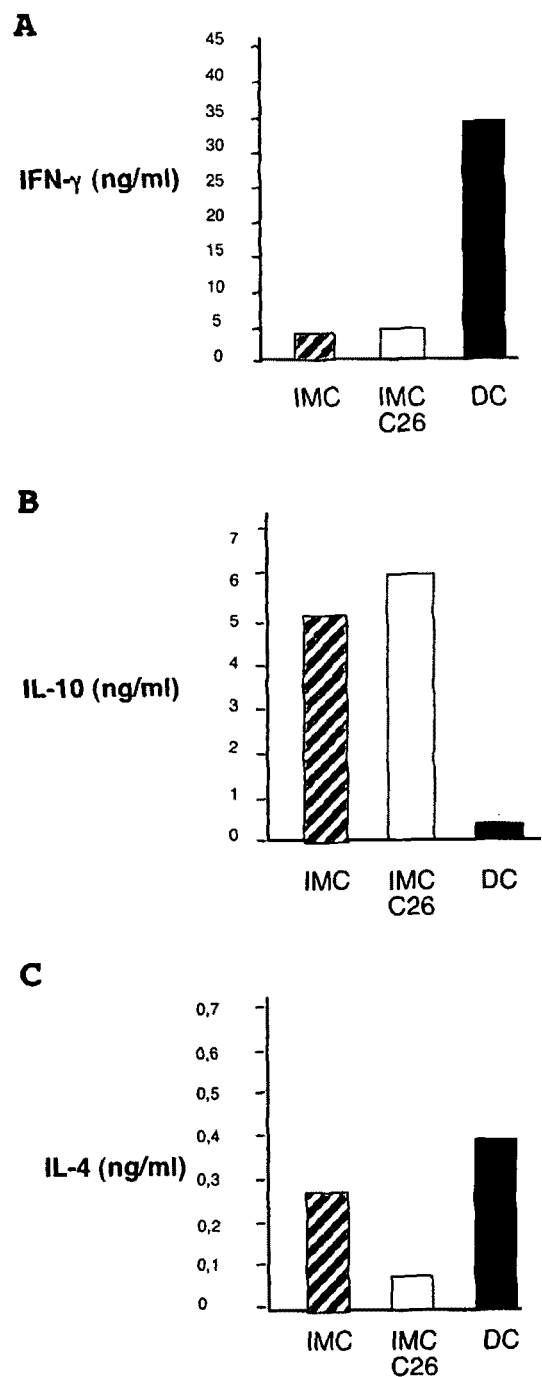
FIGS. 5A, 5B and 5C are graphs representing the expression of IFN-γ, IL-10, IL-4 and primed CD4+ cells.

We discovered that, if IMCs effectively accumulate into lymphoid organs, they further accumulate in tumor sites and this tumor accumulation operates at far greater extent than in lymphoid organs.

This specific tumor accumulation was unexpected since IMCs are very poor migrating cells like mature DCs. As an example and for DCs used in immunotherapy, it has been shown that less than 5% of intra-dermally administered mature DCs reach the draining lymph nodes (DE VRIES et al., Cancer Res., vol. 63, p: 12-17, 2003) and several approaches are developed in immunotherapy to stimulate this DC migration. Consequently, nothing suggest to one skilled in the art that IMCs are able to migrate to and to accumulate in tumor sites.

Moreover, we demonstrated that this IMC accumulation is correlated with IL-10 tumor expression. In fact, we demonstrated that a neutralizing anti-IL-10R antibody permits IMC differentiation into immature dendritic cells.

These results were also unexpected since it was thought that IL-10 does not stimulate myelopoiesis—i.e., IMC differentiation—but mostly affects relatively mature cells.

Another major factor of tumor escape from the immune system is associated with immunosupression mechanisms' activation.

The CD4+CD25+ T cells constitute nearly 10% of CD4+ T cells in naïve animals and also exist in humans (ITOH et al., J. Immunol., vol. 162, p: 5317-5326, 1999). These cells are also able to suppress CD4+ T-cell-induced organ-specific autoimmune diseases (SAKAGUCHI et al., J. Immunol., vol. 155, p: 1151-1164, 1995) and immune responses against foreign antigens and pathogens (XU et al., J. Immunol., vol. 170, p: 394-399, 2003; OLDENHOVE et al., J. Exp. Med., vol. 198, p: 259-266, 2003). In the context of tumor immunology, the CD4+CD25+ T cells have been shown to suppress anti-tumor immunity. ugmentation of CD4+CD25+ T cell number or proportion in tumor sites has been reported in variety of cancer patients (WOO et al., Cancer Res., vol. 61, p: 4766-4772, 2001; SASADA et al., Cancer, vol. 98, p: 1089-1099, 2003). This augmentation of CD4+CD25+ T cells in tumor sites may result of their expansion induction by antigen-processing dendritic cells (YAMAZAKI et al., J. Exp. Med., vol. 168, p: 235-247, 2003).

The depletion of CD4+CD25+ T cells in vivo by an anti-CD25 antibody before tumor challenge enhances natural tumor immuno-surveillance and induces rejection of multiple immunogenic tumors in multiple strains of mice (ONIZUKA et al., Cancer Res., vol. 59, p: 3128-3133, 1999; GOLGHER et al., Eur. J. Immunol., vol. 32, p: 3267-3275, 2002). However, if different studies show that removing CD4+CD25+ T cells enhances anti-tumor immunity, sometimes this treatment also induces autoimmune disease (TAGUCHI et al., Eur. J. Immunol., vol. 26, p: 1608-1612, 1996; JONES et al., Cancer Immun., vol. 2, p: 1, 2002).

There is also a recognized and permanent need in the art for new reliable method for neutralizing or diminishing immunosuppression to enhance anti-tumor immunity. We thus provide a composition for inducing IMCs differentiation within the tumor sites to locally neutralize or diminish the immunosuppression.

Unexpectedly, we also found that an in vitro amplification of $CD4^+CD25^+$ T cells is induced by IMC. Consequently, the IMC tumor accumulation should explain the known $CD4^+CD25^+$ T tumor accumulation.

The constant turnover of blood cells requires the upregulation of proliferation and differentiation events in the hematopoietic tissues resulting in the production of committed progenitors to each of the eight blood lineages. Interleukin-3 (IL-3) has the broadest target specificity of all the hematopoietic growth factors and plays a central role in the production of macrophages, neutrophils, and eosinophils through stimulation of the pluripotent hematopoietic stem cells and their derivatives (BARREDAA et al., *Developmental and Comparative Immunology*, vol. 28, p: 509-554, 2004). IL-3 together with other inflammatory cytokines like TNF-α and IFN-γ may stimulate surface molecules expression like E-selectin and IL-8, that may in turn facilitate neutrophil transmigration through the epithelium during inflammatory processes, as well as stimulation of MHC class II expression (BARREDAA et al., 2004, above-mentioned).

We further found that the stimulation of immature dendritic cells, resulting from the differentiation of IMCs by anti-IL-10R antibody, with CpG oligonucleotides and IL-3 permits their differentiation into mature dendritic cells.

Finally, we found that the intratumoral expression of a soluble IL-10 receptor, which neutralizes IL-10, with CpG oligonucleotides and IL-3 induces the differentiation of IMC into mature dendritic cells.

We thus treat cancer by intratumoral administration to a subject, of a composition comprising:
  (i) a protein able to neutralize the binding of IL-10 to its receptor, or
  (ii) a nucleic acid encoding for the protein (i), or
  (iii) a cell transformed by the vector (ii) and expressing the protein (iii).

As a result, the tumor administration of the composition induces an IMC differentiation and consequently an inhibition of $CD4^+CD25^+$ T tumor accumulation.

As used herein, the term "subject" denotes a Mammal, such as a rodent, a feline, a canine and a primate; most preferably the subject is a human.

The protein able to neutralize the binding of IL-10 to its receptor may be selected from the group comprising antibodies directed against IL-10 or its receptor, soluble receptors of IL-10 and analogues of IL-10. Preferably, the protein is a soluble receptor of IL-10.

As used herein, antibody includes intact molecules or fragments thereof such as Fab and $F(ab')_2$ which are capable of binding to their antigen.

Example of neutralizing antibodies includes IL-10 neutralizing antibodies as described in CORINTI et al. (*J. Immunol.*, vol. 166, p: 4312-8, 2001) and IL-10R neutralizing antibodies as described in REINEKE et al. (*Protein Science*, vol. 7, 951-960, 1998). Examples of soluble receptors include IL-10 soluble receptors (the 238 amino acids of the extra-cellular domain of IL-10Rα, R&D SYSTEM). Preferably, the soluble receptor is an IL-10 soluble receptor.

As used herein "analogues" includes peptidic fragments able to neutralize the binding of the factor to its receptor and recombinant protein including such fragments.

Advantageously, the composition also comprises at least one molecule able to potentiate DC differentiation selected from the group comprising cytokines and Toll-like receptors ligands. Preferably, the composition also comprises at least one cytokine and at least one Toll-like receptors ligand.

Examples of cytokines include IL3 and TNF-α. Preferably, the composition comprises at least IL-3.

Examples of Toll-like receptors ligands include CpG nucleotides, lipopolysaccharide (LPS), monophosphoryl lipid (MPL), poly-I:C, RNA double strand (more than 30 bp long). Preferably, the Toll-like receptor ligand is CpG nucleotides.

The composition may comprise a nucleic acid vector encoding for a protein able to bind to Il-10 or to its receptor as described previously.

The nucleic acid vector contains the necessary elements for the transcription and translation of the coding sequence.

The coding sequence is operationally linked to a promoter having a constitutive or inductive expression in transfected or infected cell. Examples of adapted promoter include CMV or ferritin promoters. The promoter sequence can be operationally linked to enhancer sequences to potentiate the coding sequence expression. Examples of enhancer sequences include SV40 and CMV enhancer sequences.

The coding sequence is also linked to a polyadenylation signal, preferably to a strong polyadenylation signal like the late SV40 polyA.

The coding sequence includes an adapted signal sequence to obtain the secretion of the encoded protein.

The nucleic acid vector can include selectable markers that are active both in bacteria and in mammalian cells.

The nucleic acid vector may correspond to "naked DNA" like plasmids, cosmids or phagemids, preferably a plasmid and more preferably p310R plasmid (SEQ ID NO:1). Such a naked DNA may be injected into a tumor as described in U.S. Pat. No. 5,580,859. The composition may also comprise non lipid cationic polymers (WU and WU, *J. Biol. Chem.*, vol. 263, p: 14621-4, 1988) or liposomes (BRIGHMAN et al., *Am. J. Med. Sci.*, vol. 298, p: 278-81, 1989) which form complexes with naked DNA and enhance cellular uptake. Preferably, the "naked DNA" is injected without any non lipid cationic polymers or liposomes.

The nucleic acid vector may be a viral vector adapted for in vivo gene therapy protocols. Examples of appropriate viral vectors includes retroviral vectors as described in EP 0871459, EP 0386882 and EP 1222300 and adenovirus vectors as described in US 2004/265273 and U.S. Pat. No. 6,638, 502. In this case, the internalization of virus occurs through the specific interaction of the viral envelope with a cell surface receptor, followed by receptor-mediated endocytosis of the virus/receptor complex.

Advantageously, the nucleic acid vector also encodes at least one molecule able to potentiate DC differentiation selected in the group comprising cytokines and Toll-like receptors ligands. Preferably, the nucleic acid vector also encodes at least one cytokine and at least one Toll-like receptors ligand.

Preferably, the nucleic acid vector also encodes at least IL-3.

Preferably, the nucleic acid vector also encodes CpG nucleotides.

The composition may comprise a cell transformed with a nucleic acid vector as described previously and expressing an effective amount of a protein able to bind to Il-10 or to its receptor as described previously.

Advantageously, the cell is obtained from the subject to be treated.

The composition may comprise a vehicle. For example, the composition may comprise emulsions, microemulsions, oil-in-water emulsions, anhydrous lipids and oil-in-water emulsions, other types of emulsions. The composition may also comprise one or more additives (e.g., diluents, excipients, stabilizers, preservatives). See, generally, *Ullmann's Encyclopedia of Industrial Chemistry*, 6$^{th}$ Ed. (various editors, 1989-1998, Marcel Dekker); and *Pharmaceutical Dosage Forms and Drug Delivery Systems* (ANSEL et al., 1994, WILLIAMS & WILKINS).

The composition may comprise a buffer, water, emulsions or microemulsions. Suitable buffers include, but are not limited to, phosphate buffered saline Ca$^{++}$/Mg$^{++}$ free (PBS), phosphate buffered saline (PBS), normal saline (150 mM NaCl in water), and Tris buffer.

We provide methods of therapeutic treatment of a subject suffering from cancer comprising the step of administrating to the subject directly into the tumor an effective amount of the composition described previously.

An effective amount of a protein for inducing the neutralization of IL-10, which is implicated in a DC differentiation defect, and thus inducing IMC differentiation, depends of the used protein. These effective amounts are well known to one skilled in the art for many proteins or can be determined without undue experimentation. As an example, the effective amount of a specific IL-10 antibody for inducing the neutralization of IL-10 is at least 10 µg/ml (WAKKACH et al, *Immunity*, vol. 18, p: 605-617, 2003).

An effective amount of a molecule able to potentiate DC differentiation depends of the used molecule. These effective amounts are well known to one skilled in the art for many molecules or can be determined without undue experimentation. As an example, the DC differentiation effective amounts for CpG and IL-3 are at least 2 µM and 10 ng/ml respectively.

Our disclosure is further illustrated below by the following Examples, which are not intended to limit its scope.

EXAMPLES

1—IMC Accumulation and Tumor Development

Mice BALB/C were purchased from Charles River Laboratory (IFFACREDO). All mice were then raised in common mouse pathogen-free conditions and were 4-week-old at the beginning of the experiment. To obtain mice with induced tumors (called C26 mice), a first group of mice were injected subcutaneously with cells from the murine colon adenocarcinoma line MCA26 as described in GRI et al. (*J. Immunology*., vol. 170(1), p: 99-106, 2003).

Mononuclear cells were purified from spleen (S), liver (L) and tumors of 8-week-old mice according to the protocol described in BLIN-WAKKACH et al. (*Leukemia*, vol. 18(9), p: 1505-11, 2004). The purified cells were then incubated with labelled anti-CD11b and anti-Gr-1 Abs to identify the cells expressing the specific IMC CD11b and Gr-1 surface markers. Finally, the percentages of IMCs in these purified cells were established by flow cytometry on FACSCAN flow Cytometer® (BECTON DICKINSON) according to the manufacturer's instructions. Non-specific binding was measured using FITC-conjugated isotype-matched mouse Ig.

FIGS. 1A and 1B represent the expression pattern of CD11b and Gr-1 in Mononuclear purified cells from spleen (S) and liver (L) of normal and C26 mice, respectively. The percentages of IMCs expressing characteristic levels of CD11b and Gr-1 in spleen (S) and in liver (L) for wild type and C26 mice are indicated.

FIG. 2A represents the expression pattern of CD11b and Gr-1 in Mononuclear cells from tumors of C26 mice.

Unexpectedly, the results show that the development of tumors in C26 mice is correlated with a strong accumulation of IMCs in spleen (7.5% versus 1.9%) and in liver (11.5% versus 1.4%). Moreover, this accumulation of IMCs specifically in tumor is even stronger (24%). Thus, these results show for the first time that IMCs are able to migrate and to accumulate at a high level in tumors.

2—IMC and Natural Regulatory T Cell Tumor Accumulation

Mononuclear cells were purified from tumors as described previously. The cells were then incubated with labelled anti-CD25 and anti-CD4 Abs to identify the natural regulatory T cells characterized by the expression of CD4 and CD25 markers. Finally, the percentage of IMC in these cells was established by flow cytometry on FACScalibur flow Cytometer® (BECTON DICKINSON) according to the manufacturer's instructions. Non-specific binding was measured as previously.

FIG. 2B represents the pattern of expression of CD25 and CD4 in T cells from tumors of C26 mice.

Unexpectedly, the results show that the accumulation of IMC in tumor is correlated with regulatory T cells expansion and recruitment.

3—IMC Accumulation and Ageing

Mononuclear cells were purified from spleen and tumors of 33-week-old mice as described previously. The cells were then incubated with labelled anti-CD11b and anti-Gr-1 Abs to identify the IMC. Finally, the percentage of IMC in these cells was established by flow cytometry on FACSCAN flow Cytometer® (BECTON DICKINSON) according to the manufacturer's instructions. Non-specific binding was measured as previously.

FIGS. 3A and 3B represent the pattern of expression of CD11b and Gr-1 in mononuclear cells from spleen (S) of normal and C26 33-week-old mice, respectively.

FIG. 3C represent the pattern of expression of CD11b and Gr-1 in mononuclear cells from tumors of C26 33-week-old mice.

The percentages of IMC expressing characteristic levels of CD11b and Gr-1 in spleen (S) and in tumors are indicated.

The results show that the accumulation of IMC in spleens and in tumors is increased with ageing.

4—Induction and Expansion of Regulatory T-cells by IMC a) Naïve CD4$^+$ Cells Purification:

Naïve CD4$^+$ cells have been prepared from homozygous DO11.10 transgenic mice obtained from N. Glaishenous (INSERM) as described in WAKKACH et al. (2003, abovementioned). These transgenic mice express a specific Ovalbumin T receptor.

b) In vitro IMC Expansion:

Simultaneously, mononuclear cells were purified from spleen of normal and C26 mice as described previously. The purified cells were cultured with RPMI (INVITROGEN), 5% of SVF (HYCLONE; PERBIO) in the presence of interleukin 3 (IL-3)(10 ng/ml) for twelve days long to amplify IMCs.

FIGS. 4A and 4B represent the expression pattern of CD11b and Gr-1 in mononuclear cells immediately after purification and after twelve days of culture respectively from spleens of normal mice.

FIG. 4C represents the morphology of amplified IMC after twelve days of culture by GIEMSA coloration.

The results show that the experimental culture protocol allows obtaining cell cultures with nearly 80% of IMCs.

Thus, IMC cultures from normal and CD26 mice have been obtained with the protocol described previously.

c) Purification of Splenic DCs:

Splenic DCs have been purified as described in WAKKACH et al. (2003, above-mentioned).

d) Induction of Regulatory T 1 Cells (Tr1):

Purified naïve CD4$^+$ cells (2.5 10$^5$/ml) obtained in a) have been cultured for seven days with splenic DCs, normal or CD26 IMC culture (10$^5$/ml) and with the OVA$_{323\text{-}339}$ peptide (SEQ ID NO:2, ISQAVHAAHAEINEAGR; 0.6 μM). After differentiation, T cells were restimulated with 0.3 μM OVA$_{323\text{-}339}$ and irradiated total splenic APCs. The production of IFN-γ, IL-10, IL-4 and was measured by ELISA in supernatants collected at 48 h.

FIGS. 5A, 5B and 5C represent, respectively, the expression of IFN-γ, IL-10, IL-4 and by primed CD4$^+$ cells cultured under the different conditions described above.

The results show that the stimulation of naïve CD4$^+$ cells by normal or CD26 IMC culture induces an IL-10 strong secretion and an IFN-γ low secretion, which are characteristic of regulatory T cells (Tr1).

e) Expansion of Natural Regulatory T Cells (CD4$^+$ CD25$^+$):

The natural regulatory T cells were purified by FACS sorter FACS VANTAGE (Becton-dickson) from spleens of homozygous DO11.10 transgenic mice based on the expression of CD4 and CD25 (CD4$^+$ CD25$^+$ regulatory T cells: Treg cells).

FIG. 6A represents the expression of CD24 and CD25 by the spleen cells of homozygous DO11.10. The 4.5% of regulatory T cells are framed.

Simultaneously, IMC from C26 mice were purified by FACS Vantage as described previously.

Then, 2.5 10$^5$/ml of Treg cells have been cultured for tree days with IMC (10$^5$/ml), and with the OVA$_{323\text{-}339}$ peptide (0.6 μM).

FIG. 6B represent the expression of CD62L and CD25—i.e., Tr1 cell markers—after three days of culture.

The results show that IMC were able to expand the Treg cells according to the CD62L cells expression. In fact, the regulatory T cells have strongly proliferated (from 2.5 10$^5$/ml to 2.5 10$^6$/ml) in these conditions—i.e., 10 fold more.

Figure 7:
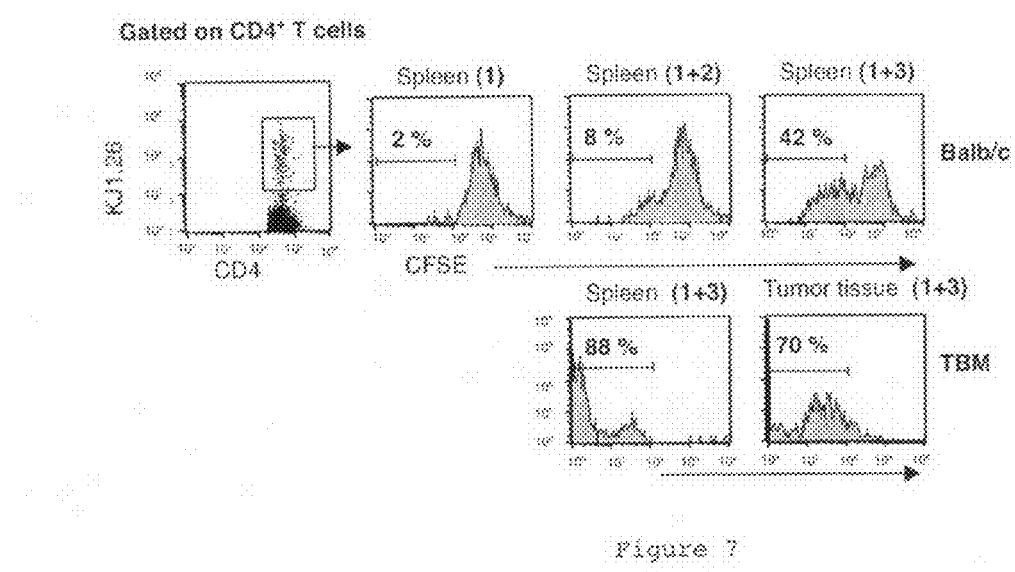
FIG. 7 graphically shows that CFSE-labeled splenic OVA-specific CD4+CD25+ Treg cells from D011-10 mice transferred into normal Balb/c mice or mice bearing C26 tumors were able to proliferate in vivo in the presence of purified IMC's from mice bearing C26 tumors pulsed with OVA peptide.

FIG. 7 shows that CFSE-labeled splenic OVA-specific CD4$^+$CD25$^+$ Treg cells from DO11-10 mice transferred into normal Balb/c mice or mice bearing C26 tumors were able to proliferate in vivo in the presence of purified IMCs from mice bearing C26 tumors pulsed with OVA peptide.

In conclusion, IMCs induces the specific differentiation of naïve CD4$^+$ cells into Tr1 cells and expand the natural Treg in vitro and in vivo.

The contribution of IL-10 in the expansion of natural Treg elicited by IMCs from mice bearing C26 tumors has been confirmed by neutralizing mouse IL-10 with an anti-IL10 receptor antibody.

5—IL-10 and IMC Accumulation a) IMC Purification and Culture

Purified mononuclear cells from spleens of normal and IL-10$^{-/-}$ mice were cultured with interleukin 3 (IL-3) for twelve days long as described previously.

FIGS. 8A and 8B show the morphology of the cells after twelve days of culture by GIEMSA coloration.

As described previously, IMCs were obtained after twelve days of culture of normal mice purified mononuclear cells (cf. FIG. 8A). For IL-10$^{-/-}$ mice mononuclear cells, the IMCs were differentiated into dendritic cells after twelve days of culture (FIG. 8B).

Consequently, these results show that the IL-10 expression is critical for the IMC immature state maintenance.

b) Induction of Tr1 or Th1 Cells

Purified naïve CD4$^+$ cells have been cultured for three days with DCs obtained from IL-10$^{-/-}$ mice or IMC culture and with the OVA$_{323\text{-}339}$ peptide as described previously. The supernatant secretion of IL-10 and IFN-γ was then measured by ELISA.

FIGS. 10A and 10B represent, respectively, the expression of IFN-γ and IL-10 by naïve CD4$^+$ cells cultured under the different conditions described above.

The results show that the stimulation of naïve CD4$^+$ cells by DCs obtained from IL-10$^{-/-}$ mice induces an IFN-γ strong secretion, which are characteristic of Th1 cells. At the same time, the stimulation of naïve CD4$^+$ cells by IMC culture induces an IL-10 strong secretion and an IFN-γ low secretion as previously.

c) IMC Culture with an Anti-IL-10R Antibody

Purified mononuclear cells from spleens of normal mice were cultured with IL-3 for twelve days long and with or without a neutralizing anti-IL-10R antibody (R&D SYSTEM) and nucleic acids with (2 μM) of CpG dinucleotides 1826, (5' TCC ATG ACG TTC CTG ACG TT 3'; SEQ ID NO:3) during the last two days.

FIGS. 9B and 9A represent the pattern of expression of CD11c and Gr-1 in the amplified IMC cells from spleen (S) of normal and C26 mice at the end of the twelve days with or without anti-IL-10R antibody and CpG dinucleotides, respectively.

Consequently, these results confirm that IL-10 expression is critical for the IMC immature state maintenance.

6—In vivo IMC Maturation Induction a) p310 R Plasmid Construction:

T cells derived from BALB/C mice splenocytes were cultured for 12 hours long in RRPMI medium (LIFE TECHNOLOGIES) with 1 μg/ml of concanavalin A.

Total RNA was extracted from 2.10$^6$ cells using NUCLEOSPIN RNA2® (MACHEREY NAGEL) according to manufacturer's instructions. Single-strand cDNAs was synthesized from 1 μg of total RNA using oligo-dT primers and M-MLV Reverse Transcriptase (PROMEGA) according to the supplier's protocol. The soluble fragment of mouse IL-10 R (NM_034686, N-term 275 amino acids, SEQ ID NO:4) was amplified with probest-DNA polymerase (TAKARA) according to the manufacturer's instructions using sense (IL-10Rs S (SEQ ID NO:5): 5'-TCT AGA GAT GTT GTC GCG TTT GCT CC-3') and antisense (IL-10Rs AS (SEQ ID NO:6): 5'-CCT AGG CTA AGT GAA ATA CTG CTC CGT CG-3') primers containing XbaI and AvrII restriction sites (bold), respectively.

PCR program was as follows:

| Step 1 (1 round):  | 94° C. | 2 minutes   |
|--------------------|--------|-------------|
| Step 2 (35 rounds):| 94° C. | 30 seconds  |
|                    | 58° C. | 40 seconds  |
|                    | 72° C. | 1 minutes   |
| Step 3 (1 round):  | 72° C. | 10 minutes. |

The IL-10Rs PCR product and pVIVO2-mcs (INVIVOGEN) were digested with XbaI and AvrII restriction enzymes (BIOLABS). Then, the digested IL-10Rs PCR product was subcloned into XbaI-AvrII-cleaved pVIVO2-mcs. The resulting recombinant expression plasmid (designated pVIVO2-IL-10Rs) was sequenced to ensure that the insertion was cloned correctly.

The complete mouse IL-3 (NM_010556, complete IL-3 protein SEQ ID NO:7) was amplified as described previously from single-strand cDNA using sense (IL-3 S (SEQ ID NO:8): 5'-CCA TGG AGA CAA TGG TTC TTG CCA GC-3') and antisense (IL-3 AS (SEQ ID NO:9): 5'-GGA TCC TTA ACA TTC CAC GGT TCC ACG-3') primers containing NcoI and BamHI restriction sites (bold), respectively.

The IL-3 PCR product and the pVIVO2-IL-10-Rs plasmid were digested with Nco I and Bam HI restriction enzymes (BIOLABS) according to the supplier's protocol. Then, the digested IL-3 PCR product was subcloned into NcoI-BamHI-cleaved pVIVO2-IL-10Rs. The resulting recombinant expression plasmid (designated p310R, SEQ ID NO:1) was sequenced to ensure that the insertion was cloned correctly. FIG. 11 represents the p310R sequence wherein IL-10 and IL-3 sequences are underlined and in bold, respectively.

b) Transient Transfection of IMC Cell Line Established in Our Laboratory:

IL-3 and IL-10Rs expression are tested in vitro by transiently transfecting GPM-45 cell line cells using Lipofectamine (INVITROGEN) according to the manufacturer's instructions. GPM-45 is an IMC cell line obtained in the laboratory by the isolation of cells expressing CD11b and Gr-1 from a tumor of a p53$^{-/-}$ transgenic mouse. The expression of IL-10Rs and IL-3 were determined by testing the presence of these proteins in the supernatant by using two ELISA kits for detecting IL-10Rs and IL-3 (BECTON-DICKINSON) respectively.

c) In vitro IMC Cells Differentiation:

Mononuclear cells were purified from spleens of normal and C26 mice as described previously. The purified cells were cultured with interleukin 3 for 12 days long to amplify IMCs.

Then, IMCs cells were transfected using LIPO-FECTAMINE® (Invitrogen) according to the manufacturer's instructions with one of the following construction: (1) p310R vector; (2) pVIVO-IL-10Rs vector; (3) pVIVO2 vector; (4) no plasmid DNA.

The transfected cells were cultured for further seven days in the culture medium without IL-3, and in the presence of hygromycin.

5—In vivo Expression of p310R Plasmid Induces IMC Maturation into DCs at Tumor Site 9 stable clones transfected with p310R were selected after three months of culture, including the clone C-26p310R.

The expression of IL-3 and IL-10Rs mRNAs in the clones has been confirmed by RT-PCR.

At the time, a stable C26-pVIVO2 clone was selected.

$5.10^5$ C-26p310R and C26 cells were injected subcutaneously to two mice groups (n=10), respectively.

Figure 12:
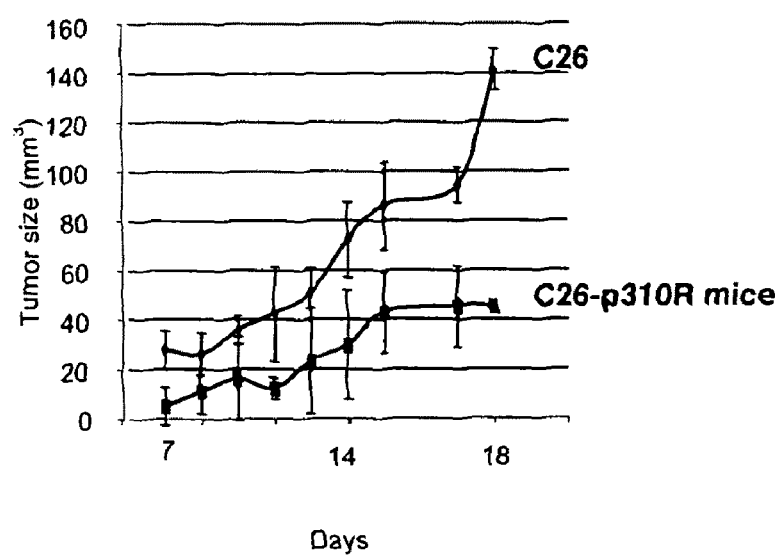
FIG. 12 is a graph showing that the IL-10Rs and IL-3 expression in C-26p310R cells inhibits tumor growth by more than three fold.

The result shows that the IL-10Rs and IL-3 expression in C-26p310R cells inhibits tumor growth by more than three fold (see FIG. 12).

Figure 13:
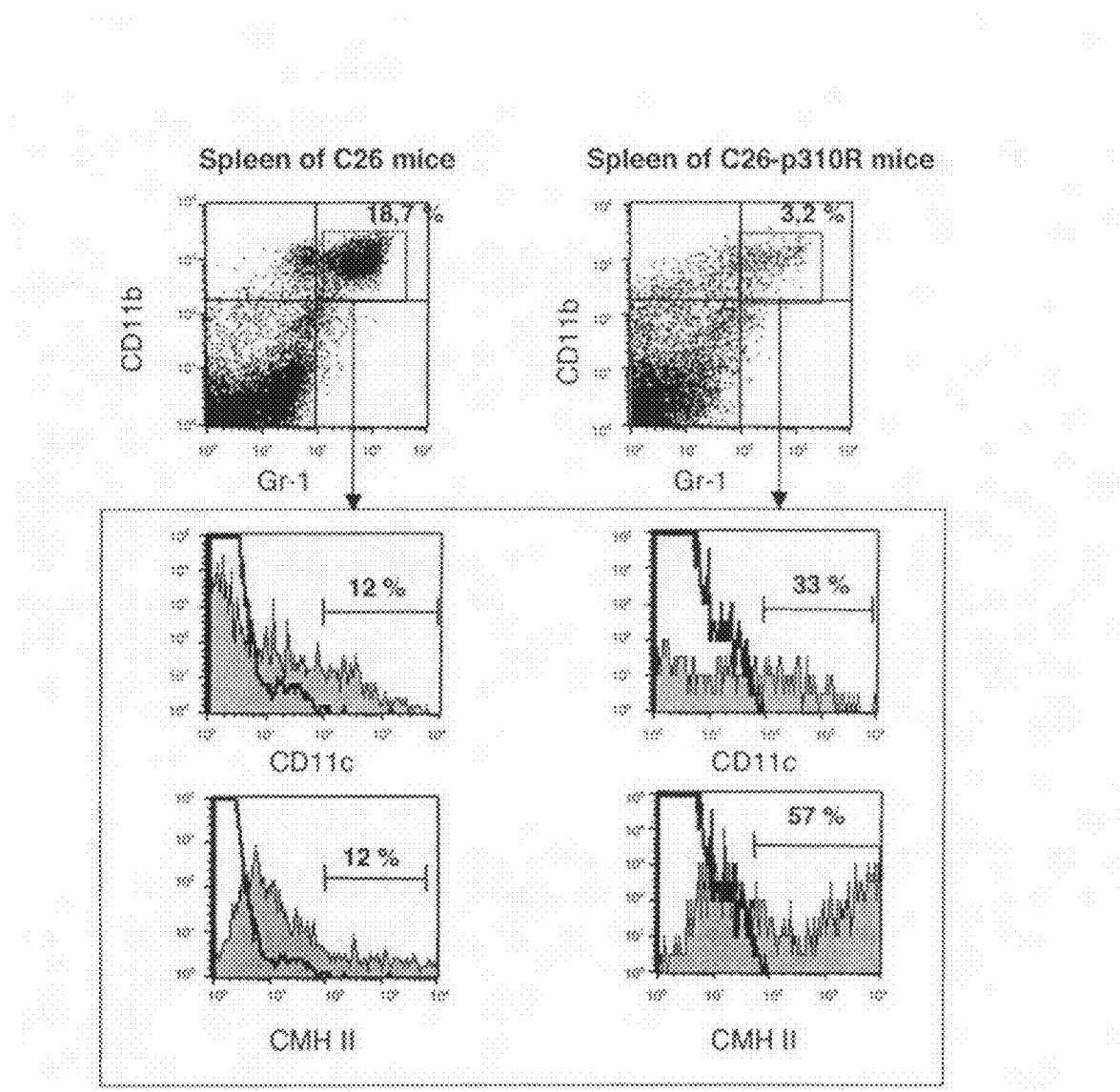
FIG. 13 graphically shows that the expression IL-3 and IL-10Rs in the tumor inhibits IMC accumulation simultaneously in the tumor and in the spleen and stimulates their differentiation into DCs mature secreting IL-12p70 and interferon gamma: two cytokines involved in anti-tumoral immune response.

Interestingly, the results have also shown that the expression IL-3 and IL-10Rs in the tumor inhibits IMC accumulation simultaneously in the tumor and in the spleen and stimulates their differentiation into DCs mature secreting IL-12p70 and interferon gamma: two cytokines involved in anti-tumoral immune response (see FIG. 13 and Table I below).

TABLE I

| Cytokines expression in Splenic CD11c cells | | | | |
|---|---|---|---|---|
| ng/ml | C26 + LPS | C26 + CpG | C26-p310 + LPS | C26-p310R + CpG |
| IL-10 | 3.7 | Nd | 1.4 | 1.9 |
| IL-12p70 | Nd | Nd | Nd | 5.2 |
| IFN-γ | 2.7 | Nd | 3.7 | 4.3 | e) Intra-Tumoral Administration of IL-3 and IL-10Rs:

C26 mice are divided randomly into four groups, and each group consists of 10 mice that are injected intratumoraly with one of the following regimens in 100 μl of sterilized normal saline: (1) 100 μg of p310R vector; (2) 100 μg of pVIVO-IL-10Rs vector; (3) 100 μg of pVIVO2 vector; (4) no plasmid DNA. The mice in the last group serve as a challenge infection control. Tumors evolution is controlled in each group following the injection.

Tumor growth is monitored by palpation and measurement using a Calipar three times a week as previously described (GRIC et al., 2003, above-mentioned).

The invention claimed is:

1. A method of treating cancer comprising: intratumorally administering a therapeutically effective amount of a composition comprising:
   (i) a protein able to neutralize the binding of IL-10 to its receptor that is a soluble receptor for IL-10, an IL-3 protein, and a Toll-like receptor ligand, or
   (ii) a nucleic acid encoding the protein able to neutralize the binding of IL-10 to its receptor that is a soluble receptor for IL-10 and encoding the IL-3 protein, and a Toll-like receptor ligand, or
   (iii) a cell transformed by the nucleic acid (ii) and expressing the protein able to neutralize the binding of IL-10 to its receptor that is a soluble receptor for IL-10 and expressing the IL-3 protein, and a Toll-like receptor ligand, to a patient.

2. The method according to claim 1 wherein the Toll-like receptor ligand is a CpG nucleotide.

3. A method of treating cancer comprising: intratumorally administering a therapeutically effective amount of a composition comprising:
   (i) a protein able to neutralize the binding of IL-10 to its receptor, and an IL-3 protein, or
   (ii) a nucleic acid encoding a protein able to neutralize the binding of IL-10 to its receptor and encoding an IL-3 protein, or
   (iii) a cell transformed by the nucleic acid (ii) and expressing a protein able to neutralize the binding of IL-10 to its receptor and expressing an IL-3 protein, to a patient.

4. A method of treating cancer comprising: intratumorally administering a therapeutically effective amount of a composition comprising:
   (i) a nucleic acid encoding a protein able to neutralize the binding of IL-10 to its receptor wherein the nucleic acid comprises SEQ ID NO: 1, or
   (ii) a cell transformed by the nucleic acid (i) and expressing a protein able to neutralize the binding of IL-10 to its receptor,
to a patient, wherein the composition optionally comprises a molecule able to potentiate dendritic cell differentiation selected from the group consisting of a cytokine and a Toll-like receptor ligand.

5. The method according to claim 4 wherein the Toll-like receptor ligand is a CpG nucleotide.

* * * * *